United States Patent

Meyer

(10) Patent No.: US 11,504,176 B2
(45) Date of Patent: Nov. 22, 2022

(54) PEDICLE SCREW PLACEMENT SYSTEM AND METHOD FOR SPINAL SURGERY

(71) Applicant: Paragon Spine, Inc., Gainesville, FL (US)

(72) Inventor: Scott Meyer, Orlando, FL (US)

( * ) Notice: Subject to any disclaimer, the term of this patent is extended or adjusted under 35 U.S.C. 154(b) by 168 days.

(21) Appl. No.: 16/738,940

(22) Filed: Jan. 9, 2020

(65) Prior Publication Data

US 2020/0138493 A1    May 7, 2020

Related U.S. Application Data

(60) Division of application No. 15/243,829, filed on Aug. 22, 2016, now Pat. No. 10,561,455, which is a continuation of application No. PCT/US2016/047913, filed on Aug. 19, 2016.

(60) Provisional application No. 62/208,112, filed on Aug. 21, 2015.

(51) Int. Cl.
*A61B 17/70* (2006.01)
*A61B 17/86* (2006.01)

(52) U.S. Cl.
CPC ........ *A61B 17/863* (2013.01); *A61B 17/7058* (2013.01); *A61B 17/864* (2013.01)

(58) Field of Classification Search
CPC ............ A61B 17/7058; A61B 17/7083; A61B 17/7059; A61B 17/8038
See application file for complete search history.

(56) References Cited

U.S. PATENT DOCUMENTS

| | | | | |
|---|---|---|---|---|
| 5,569,251 A * | 10/1996 | Baker | ................... | A61B 17/80 606/281 |
| 6,235,034 B1 * | 5/2001 | Bray | .................. | A61B 17/1757 606/295 |
| 7,481,829 B2 * | 1/2009 | Baynham | ............. | A61B 17/686 606/327 |
| 8,690,931 B2 * | 4/2014 | Appenzeller | ........ | A61B 17/861 606/257 |
| 9,339,316 B2 * | 5/2016 | Hulliger | ............. | A61B 17/8685 |
| 2003/0208203 A1 * | 11/2003 | Lim | ..................... | A61B 17/808 606/86 A |
| 2004/0030336 A1 * | 2/2004 | Khanna | .............. | A61B 17/8038 606/86 B |
| 2004/0210217 A1 * | 10/2004 | Baynham | ........... | A61B 17/8635 606/295 |
| 2005/0033294 A1 * | 2/2005 | Garden | .............. | A61B 17/7059 623/17.11 |
| 2006/0195099 A1 * | 8/2006 | Bottlang | ............ | A61B 17/8605 606/67 |
| 2008/0183220 A1 * | 7/2008 | Glazer | ................. | A61B 17/686 606/301 |
| 2008/0288003 A1 * | 11/2008 | McKinley | .......... | A61B 17/8625 606/301 |

(Continued)

*Primary Examiner* — Jan Christopher L Merene
(74) *Attorney, Agent, or Firm* — Ashkan Najafi

(57) ABSTRACT

Spinal pedicle screws are placed into vertebrae from the same approach and the same anterior, anterolateral or anterior/lateral exposure that is used for an anterior/lateral spine operation, during the same surgical procedure as the spine operation. Once the anterior spine operation is complete, pedicle screws areplaced into the vertebrae with a front-to-back trajectory, in a generally anterior, lateral, anterolateral, or contralateral trajectory, avoiding the need for a second operation exposing the posterior spine.

9 Claims, 15 Drawing Sheets

(56) References Cited

U.S. PATENT DOCUMENTS

| | | | |
|---|---|---|---|
| 2009/0036933 A1* | 2/2009 | Dube | A61B 17/808 606/282 |
| 2009/0157123 A1* | 6/2009 | Appenzeller | A61B 17/68 606/301 |
| 2011/0144700 A1* | 6/2011 | Konieczynski | A61B 17/8042 606/289 |
| 2012/0022600 A1* | 1/2012 | Overes | A61B 17/8004 606/286 |
| 2012/0265250 A1* | 10/2012 | Ali | A61B 17/7001 606/279 |
| 2013/0245697 A1* | 9/2013 | Hulliger | A61B 17/8685 606/281 |
| 2014/0142639 A1* | 5/2014 | Vennard | A61B 17/863 606/291 |
| 2015/0100126 A1* | 4/2015 | Melkent | A61F 2/442 623/17.16 |

\* cited by examiner

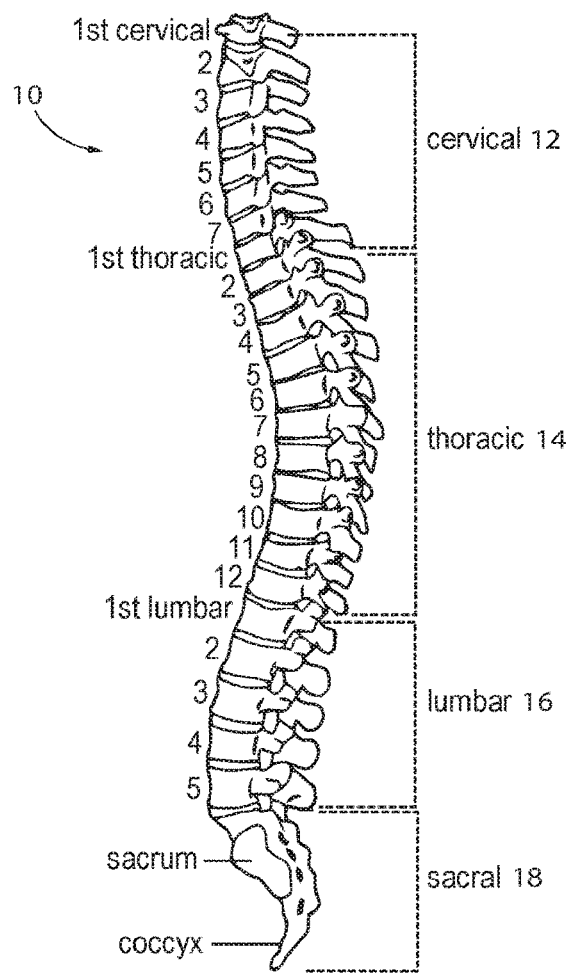
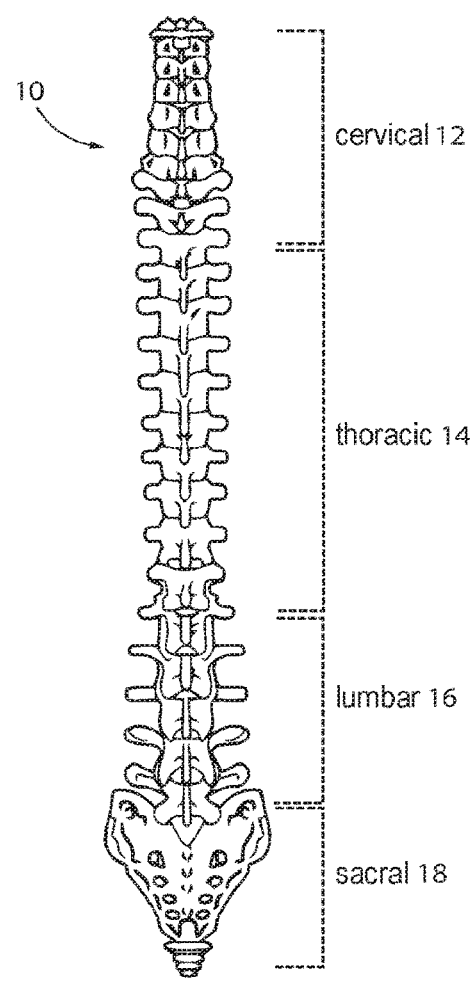
FIG. 1A
(PRIOR ART)
FIG. 1B
(PRIOR ART)

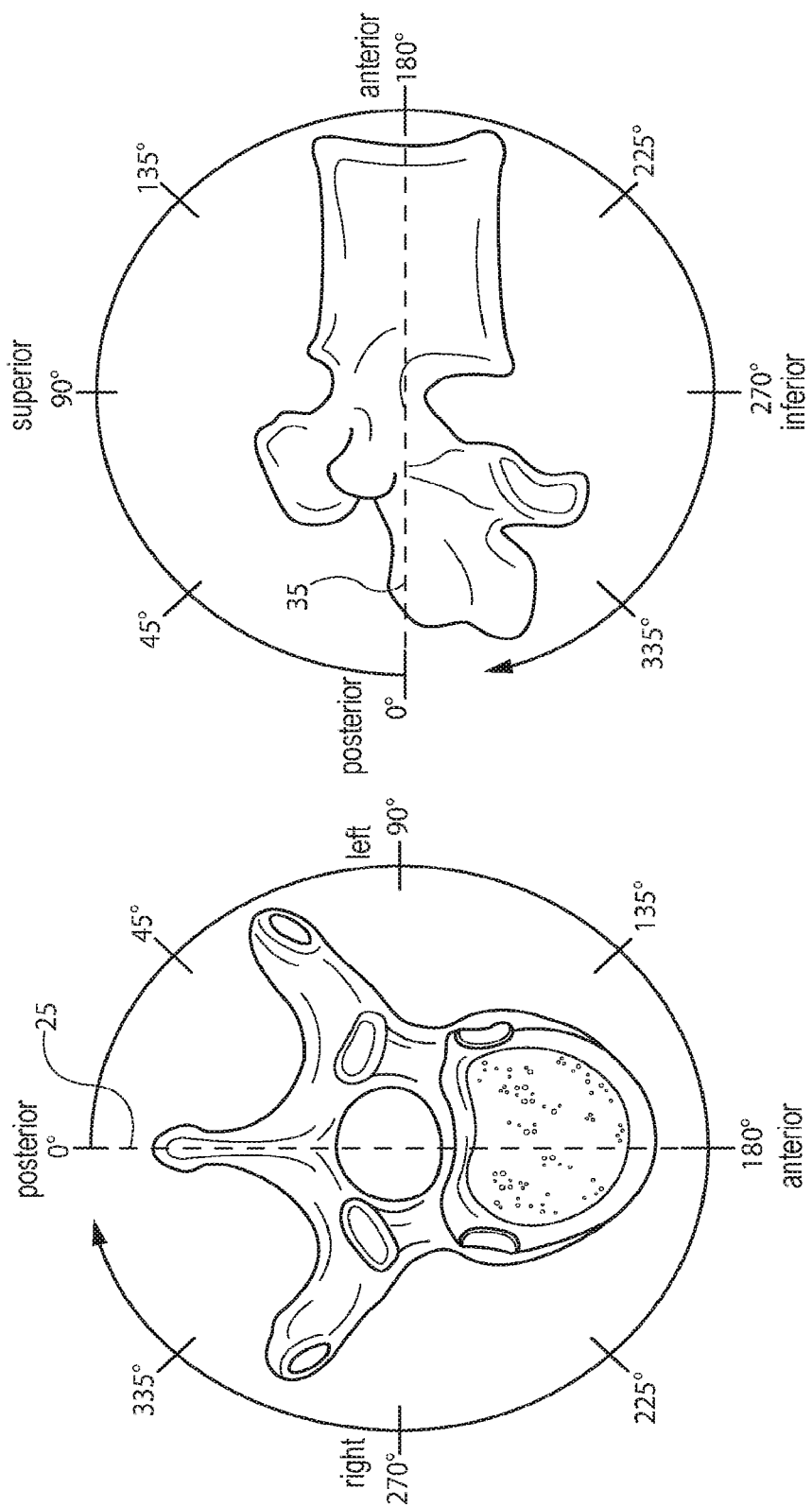

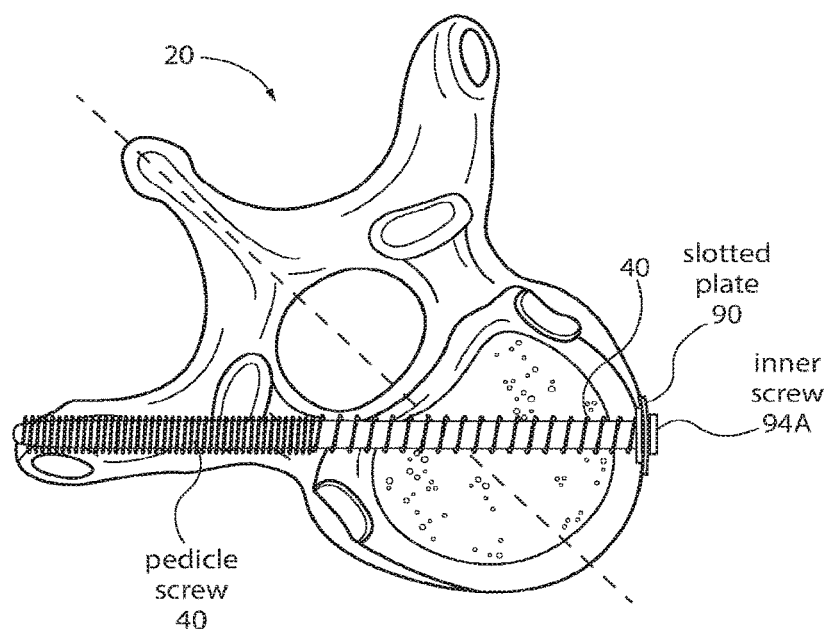
FIG. 20
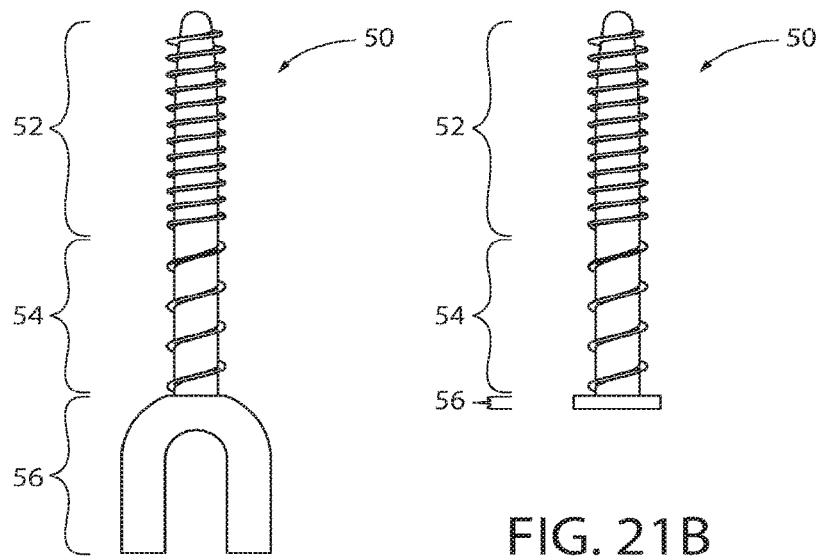
FIG. 21A
FIG. 21B
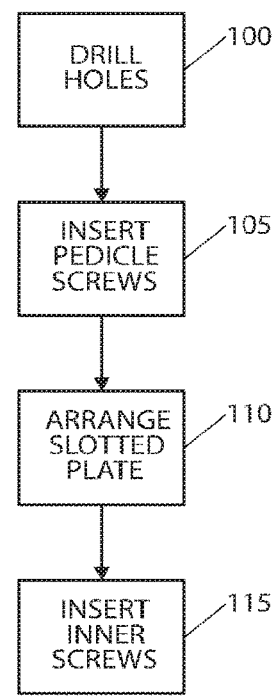
FIG. 22

PEDICLE SCREW PLACEMENT SYSTEM AND METHOD FOR SPINAL SURGERY

RELATED APPLICATION

This is a divisional patent application which claims priority to and benefit of U.S. non-provisional patent application Ser. No. 15/243,829, filed Aug. 22, 2016, currently pending, which claims priority to and benefit of U.S. provisional patent application No. 62/208,112, filed Aug. 21, 2015, now abandoned, and is a bypass continuation of international application no. PCT/US2016/0047913, filed on Aug. 19, 2016, now abandoned, which claims priority to and benefit of U.S. provisional patent application No. 62/208, 112, filed Aug. 21, 2015, now abandoned, each of which is incorporated by reference herein in its entirety.

BACKGROUND

Field of the Invention

The subject matter disclosed herein generally relates to spinal surgery techniques and more particularly relates to a system and method for placement of pedicle screws during spinal surgery for attachment to fixation devices such as plates and rods.

Related Art

Pedicle screws are used to correct deformity, and/or treat trauma. Similar to other bone screws, pedicle screws may be used in instrumentation procedures to affix rods and plates to the spine. The screws may also be used to immobilize part of the spine to assist fusion by holding bony structures together.

Although pedicle screws are most often used in the lumbar (lumbosacral) spine, they can be implanted in the thoracic and sacral vertebra. The surgeon uses fluoroscopy or conventional x-ray to determine the depth and angle for screw placement. A receiving channel is drilled in the bone of the vertebrae and the screw is threaded into the receiving channel.

Stabilization of the spine for various pathological conditions often requires a "360 degree" fixation to achieve optimal biomechanical strength in order to improve mobilization and bony fusion rates as well as reducing pain and reducing risk of complications. 360 degree fixation currently requires a two stage process comprising a first surgery for anterior inter body fusion and a second surgery for posterior column stabilization and fusion. Initially, the first surgery is performed approaching the spine from an anterior, anterolateral, or lateral exposure to stabilize the anterior column (i.e. the intervertebral space). Subsequently, on the same day or at a later date, the second surgery is performed approaching the spine from a posterior exposure to add support and make sure that the spine is sufficiently stabilized. In the second surgery, the posterior spine is exposed and approached using open or minimally invasive surgery to place instrumentation in the form of pedicle screws placed in a posterior to anterior trajectory through the pedicle and into the spine to provide supplemental spine stabilization. This second surgery to place the pedicle screws improves the biomechanical strength of the 360 degree fixation, and provides improved fusion rate, and reduced complications. However, the need for a second extensive spine operation adds a considerable amount of surgical time and recovery time, risk, pain, cost and inconvenience to the patient, even when performed with minimally invasive techniques. Therefore, what is needed is a system and method that overcomes these significant problems found in the conventional systems as described above.

SUMMARY

According to one aspect, a method of stabilization of the spine through a single surgical exposure and approach in a single operation is provided. In the single surgery, pedicle screws are placed into the spine and then the pedicle in a generally anterior, anterolateral, lateral, diagonal, and/or transverse-to-posterior trajectory. The single surgery advantageously avoids the need for a second operation exposing the posterior spine to stabilize the spine.

In one aspect, the anterior, anterolateral or anterior/lateral spine is first exposed in a similar manner to a conventional initial spinal fusion or other spinal stabilization surgery, and subsequent to the initial stabilization, pedicle screws are placed through the spine into selected pedicles from the front to the back, in a generally anterior, anterolateral, lateral, diagonal, and/or transverse-to-posterior trajectory. The pedicle is known to be the strongest part of the spine for stabilization purposes, thus this direction of insertion of a pedicle screw adds strength to the subsequent stabilization using the pedicle screws with appropriate fixation devices such as plates or rods.

The above method for pedicle screw placement may be used for stabilization of sacral, lumbar, thoracic and cervical spine regions, with appropriate adjustment of pedicle screw lengths and transverse and sagittal angles of approach based on the size of the individual vertebra. The anterior-to-posterior pedicle screw fixation and bi-cortical purchase of the placed pedicle screws in the fixation assembly provides enhanced biomechanical strength and stabilization of all three columns of the spine via a single operation and a single spinal exposure on a single side only. Fluoroscopy and/or intraoperative neuro-navigation may be used to guide screw placement, for example using a neuro-surgical navigation and imaging system as used for minimally invasive procedures.

In another aspect, a system comprises one or more pedicle screws where each pedicle screw has a first end (piercing tip) and a second end (head) and a body section between the first and second ends. The one or more pedicle screws each comprising a cortical pitch portion of the body proximal the first end of the pedicle screw and a coarse pitch portion of the body proximal the head of the pedicle screw. The system also includes one or more fixation devices configured to attach to the head of the pedicle screw.

One or more of the pedicle screws may also include a threaded inner channel configured to receive an inner screw having a body with a first diameter and a headwith a second diameter that is greater than the first diameter of the body. The inner screw is configured to be threaded into the inner channel and the system may also include a fixation device that includes at least one through hole having a diameter configured to allow the body of the inner screw to pass through and prevent the head of the inner screw from passing through the through hole.

Advantageously, the cortical pitch portion of the pedicle screw body is configured to engage the cortical bone of a pedicle when the pedicle screw is placed into a vertebra at a predetermined entry point on an anterior surface of the vertebra.

In another aspect, a method for spinal stabilization includes exposing a selected area of a spine from an anterior, anterolateral or lateral approach and subsequent to completion of a first stage of spinal stabilization surgery, placing a first pedicle screw in a first vertebra of the previously exposed selected area of the spine, the first pedicle screw having a predetermined entry point on the surface of the first vertebra and a projected exit point on the surface of the first vertebra, wherein the entry point is more anterior than the exit point to provide an anterior to posterior trajectory for the first pedicle screw.

The method may also include placing a second pedicle screw in the first vertebra where each of the first and second pedicle screws follow ipsilateral paths having respective entry points on opposite sides of a central axis of the first vertebra in a transverse plane. Alternatively, one of the first and second pedicle screws may follow a contralateral path. Alternatively, the trajectories of the first and second pedicle screws maybe transverse such that their trajectories cross from an axial planar viewpoint.

Additionally, the trajectory of the first pedicle screw may follow a predetermined first angle with respect to a transverse plane of the first vertebra and a predetermined second angle with respect to a sagittal plane of the first vertebra, where the first angle is in the range from 95° to 265° and the second angle is in the range from 170° to 200°.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 1A is a sagittal view diagram of a spine according to the prior art.

FIG. 1B is a posterior view diagram of a spine according to the prior art.

FIG. 5A is an axial planar view of a vertebra with a superimposed angle of entry determination overlay.

FIG. 5B is a sagittal view of a vertebra with a superimposed angle of entry determination overlay.

FIG. 20 is an axial planar view of a vertebra illustrating an example anterior to posterior placement from an anterolateral approach of a pedicle screw attached to a plate by an inner screw according to an embodiment of the invention.

FIG. 21A is a plan view diagram of a distal cortical thread pitch pedicle screw according to the invention.

FIG. 21B is a plan view diagram of a distal cortical thread pitch pedicle screw according to the invention.

FIG. 22 is a flow diagram illustrating an example process for connecting two pedicle screws with a plate according to the invention.

DETAILED DESCRIPTION

Figure 2A:
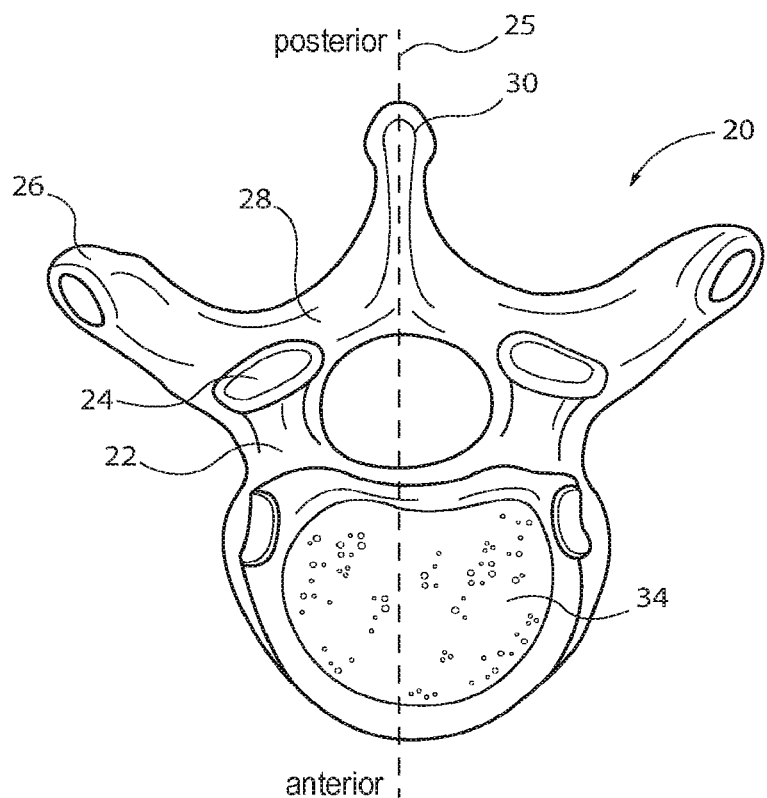
FIG. 2A is an axial planar view diagram of a vertebra according to the prior art.

The subject matter described herein is taught by way of example implementations. In portions of this description, various details have been omitted for the sake of clarity and to avoid obscuring the subject matter. The examples shown and described below are directed to a pedicle placement system and method for use in spinal surgery. After reading this description it will become apparent to one skilled in the art how to implement the invention in various alternative embodiments and alternative methods. However, although various embodiments of the present invention are described herein by way of example implementations, it is understood that these embodiments are presented by way of example only, and not limitation. As such, this detailed description of various alternative embodiments should not be construed to limit the scope or breadth of the present invention.

FIG. 1A is a sagittal view diagram of a spine 10 according to the prior art. As shown, the spine 10 comprises several regions including the cervical region 12, the thoracic region 14, the lumbar region 16 and the sacral region 18. Each region has one or more vertebra and each individual vertebra is identified by the first letter of its region and its relative position from top to bottom. For example, the sacral vertebra at the bottom of the spine is called the S1 vertebra and the lowest lumbar vertebra, which is adjacent to the S1 vertebra, is called the L5 vertebra. The L4 vertebra is adjacent to the L5 vertebra and so forth up the spine to the C1 vertebra in the cervical region.

FIG. 1B is a posterior view diagram of a spine 10 according to the prior art. In the illustration, the several regions spine 10, namely the cervical region 12, the thoracic region 14, the lumbar region 16 and the sacral region 18 are shown.

FIG. 2A is an axial planar view diagram of a vertebra 20 according to the prior art. The axial planar view is of a cross section of the vertebra 20 along the transverse plane. The plane 25 that extends from the anterior (front) side of the vertebra 20 to the posterior (back) side of the vertebra 20 and separates the vertebra 20 into left and right halves is called the sagittal plane 25. The sagittal plane 25 extends from the feet to the head of a human and, by way of example, the central sagittal plane 25 splits the human body into left and right sides.

As shown in the illustration, the vertebra 20 comprises a vertebral body 34 on the anterior side. The pedicle 22 extends from the vertebral body 34. The pedicle 22, superior articular process 24, transverse process 26, and lamina 28 form the vertebral arch 32 on each side of the vertebra 20. The spinous process 30 extends posteriorly from the lamina 28 on each side of the vertebral arch.

Figure 2B:
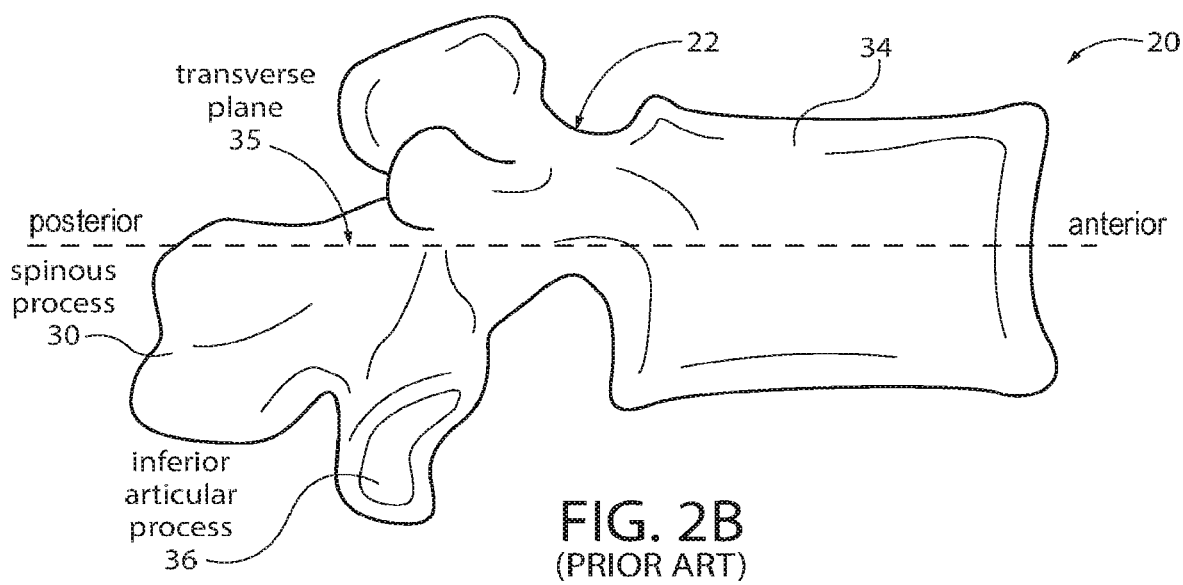
FIG. 2B is a sagittal view diagram of a vertebra according to the prior art.

FIG. 2B is a sagittal view diagram of a vertebra 20 according to the prior art. The plane 35 that extends from the anterior (front) side of the vertebra 20 to the posterior (back) side of the vertebra 20 and separates the vertebra 20 into top and bottom halves is called the transverse plane 35. The transverse plane 35 extends from the front to the back of a human and, by way of example, the central transverse plane 35 splits the human body into top and bottom halves.

As shown in the illustration, the vertebra 20 comprises a vertebral body 34 on the anterior side and the spinous process 30 on the posterior side. The vertebra 20 also includes the inferior articular process 36, which was not visible in the FIG. 2A illustration.

Figure 2C:
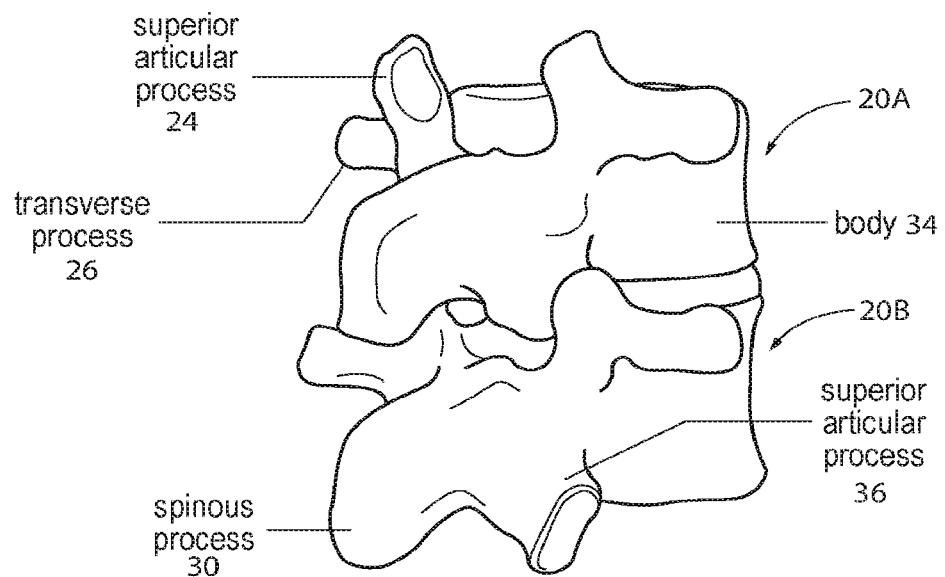
FIG. 2C is a perspective view diagram of two vertebrae according to the prior art.

FIG. 2C is a perspective view diagram of two vertebrae 20A and 20B according to the prior art. As shown in the illustration, vertebra 20A rests on top of vertebra 20B. It should be noted that certain structures identified in FIGS. 2A, 2B and 2C, such as the superior articular process 24, the transverse process 26, the spinous process 30 and the inferior articular process 36 are often used as guideposts during spinal surgery to assist in the correct placement of pedicle screws.

Figure 3:
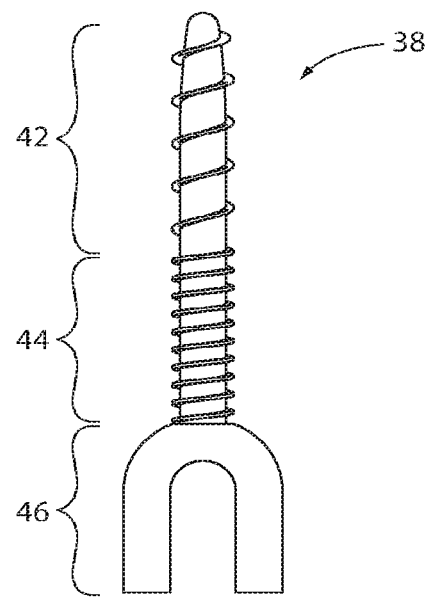
FIG. 3 is a plan view diagram of a standard thread pitch pedicle screw according to the prior art.

FIG. 3 is a plan view diagram of a standard thread pitch pedicle screw 38 according to the prior art. A standard pedicle screw such as pedicle screw 38 has head, neck and body. The head 46 is used to place the screw 38 into the bone. The threads of a pedicle screw 38 may have a cortical (short) pitch portion 44 where the threads are closer together and a coarse (long) pitch portion 42 where the threads are farther apart. The body is made up of the coarse (long) pitch portion 42 and the cortical (short) pitch portion 44. The neck is in between the head 46 and the body. The pitch of the threads determines how far the pedicle screw travels with each 360-degree turn. A standard pedicle screw 38 may have threads having a single pitch throughout the entire body section or it may have cortical threads 44 near the head 46 combined with coarse threads 42 near the end. Such an arrangement is beneficial for conventional pedicle screw placement because when fully positioned, the cortical threads are embedded in the strong pedicle bone structure of the vertebra 20 while the coarse threads are embedded in the softer body structure of the vertebra 20.

Figure 4A:
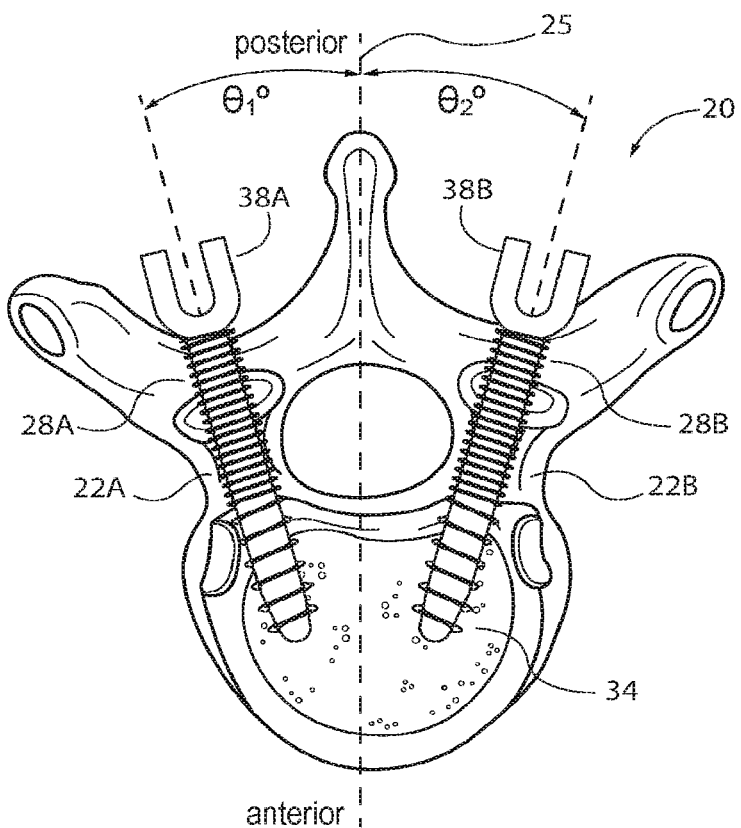
FIG. 4A is an axial planar view of a vertebra having posterior to anterior pedicle screw placement according to the prior art.

FIG. 4A is an axial planar view of a vertebra 20 having conventional posterior to anterior placement of pedicle screws 38A and 38B according to the prior art. As shown in the illustration, pedicle screw 38A enters the vertebra 20 at the lamina 28A and proceeds through the pedicle 22A and into the body 34. Similarly, pedicle screw 38B enters the vertebra 20 at the lamina 28B and proceeds through the pedicle 22B and into the body 34. As previously discussed, the illustrated screw placement takes place during a second spinal fixation surgery, following a first anterior inter body fusion surgery in which the anterior spine is exposed. For the second spinal fixation surgery, the posterior spine must be exposed.

Figure 4B:
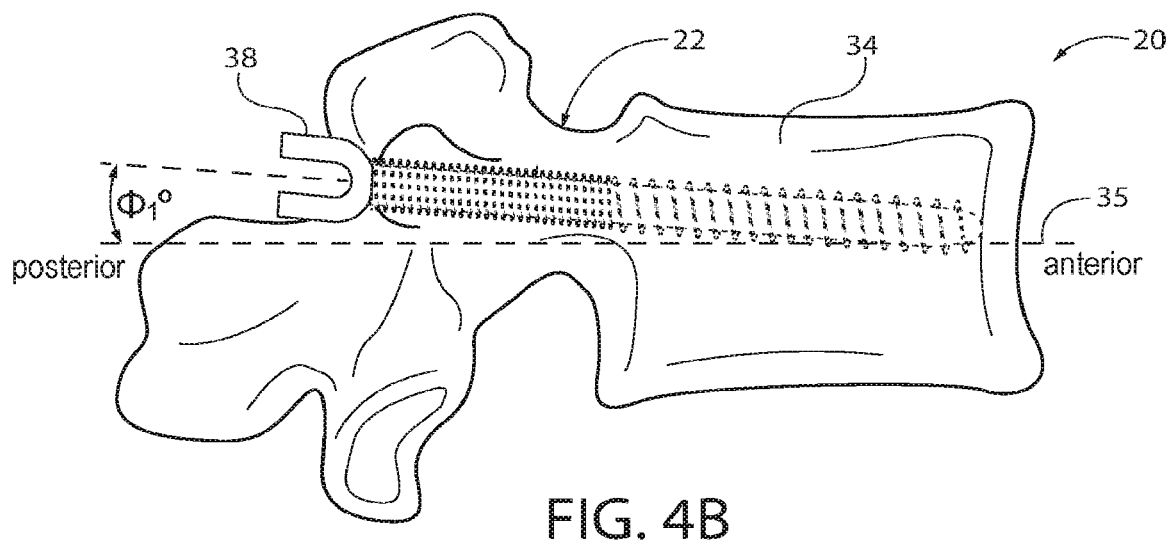
FIG. 4B is a sagittal view of a vertebra having posterior to anterior pedicle screw placement according to the prior art.

FIG. 4B is a sagittal view of a vertebra 20 having conventional posterior to anterior placement of pedicle screw 38 according to the prior art. As shown in the illustration, pedicle screw 38 enters the vertebra 20 on the posterior side of the vertebra 20 and proceeds into the body 34. As previously discussed, the illustrated screw placement takes place during a second spinal fixation surgery, following a first anterior inter body fusion surgery in which the anterior spine is exposed. For the second spinal fixation surgery, the posterior spine must be exposed.

FIG. 5A is an axial planar view of a vertebra 20 with a superimposed angle of entry determination overlay. In this description, the axial planar angle of entry may also be referred to as a trajectory, an angle of placement or simply an angle or trajectory angle. The axial planar angle of entry of pedicle screws is determined with respect to the sagittal plane 25. Starting with 0° on the posterior side and proceeding to 180° on the anterior side and so forth to 360°. Accordingly, in this description, the axial planar angles of pedicle screws will be identified using the variable θ and will be determined with respect to the entry point on the 360° overlay as shown in FIG. 5A. For example, referring back to FIG. 4A, the axial planar angle of pedicle screw 38A is in the range of about 310° to 320° or roughly about 315° and the axial planar angle of pedicle screw 38B is in the range of about 40° to 50° or roughly about 45°.

FIG. 5B is a sagittal view of a vertebra 20 with a superimposed angle of entry determination overlay. In this description, the sagittal angle of entry may also be referred to as a trajectory, an angle of placement or simply an angle or trajectory angle. The sagittal angle of entry of pedicle screws is determined with respect to the transverse plane 35. Starting with 0° on the posterior side and proceeding to 180° on the anterior side and so forth to 360°. Accordingly, in this description, the sagittal angles of pedicle screws will be identified using the variable Φ and will be determined with respect to the entry point on the 360° overlay as shown in FIG. 5B. For example, referring back to FIG. 4B, the sagittal angle $\Phi_1°$ of pedicle screw 38 is in the range of about 10° to 20° or roughly about 15°.

It should be noted that for ease of illustration in FIGS. 6-13, the labeled angles θ and Φ do not precisely illustrate the corresponding pedicle screw angle of entry and in most instances, illustrate instead the supplemental angle such that the angle of entry of the pedicle screw and the supplemental angle add up to 180°. In other instances, the illustrated angle is 180° less than the angle of entry of the pedicle screw. For example, in FIG. 8, the illustrated angle $\Phi_1°$ is the supplemental angle of the angle of entry for pedicle screw 40A and the illustrate angle $\Phi_2°$ is 180° less than the angle of entry for pedicle screw 40B such that ($\Phi_2°$+180°) equals the angle of entry for pedicle screw 40B.

Turning now to FIGS. 6-11, these figures illustrate axial planar embodiments of a pedicle screw placement system and method in which the pedicle screws are placed in an anterior to posterior direction which does not require a second operation and does not require the posterior spine to be exposed. The illustrated embodiments allow pedicle screw placement during a single anterior/lateral spine surgical operation to treat trauma, deformity, degenerative disease or the like using the same approach and the same exposure that is used for the single surgery. Instrumentation and fixation devices such as screws or rods are placed into the spine using the pedicles for stabilization, and fixation devices such as rods or plates are secured to the screws. This improves fusion rates, provides immediate stability and avoids the need for a subsequent and second invasive and extensive spine operation for pedicle screw placement.

It should be noted that in the discussion of FIGS. 6-11, an ipsilateral screw (or screw placement) is a pedicle screw placement with an entry point the vertebra 20 on one side of the sagittal plane 25 and a termination point in the vertebra 20 on the same side of the sagittal plane 25. Ipsilateral screw placements generally have an axial planar trajectory angle of approximately 140°-220°. Similarly, a contralateral screw (or screw placement) is a pedicle screw placement with an entry point the vertebra 20 on one side of the sagittal plane 25 and a termination point in the vertebra 20 on the opposite side of the sagittal plane 25. Contralateral screw placements generally have an axial planar trajectory angle of approximately 100°-260°. A transverse screw (or screw placement) is a pedicle screw that crosses over or under another pedicle screw in the same vertebra from an axial planar viewpoint.

FIGS. 6-11 illustrate several embodiments of anterior to posterior pedicle screw placement positions and trajectories through vertebral bodies at different locations in the spine, with suitable insertion points on the anterior part of the spine. The illustrated embodiments of anterior to posterior pedicle screw trajectories are suitable for use in a plurality of spinal regions, for example the S1 sacral vertebra, lumbar vertebrae including L5, L4 or higher and also the thoracic and cervical spine regions. It should be noted that above the L5 vertebra (L4 and higher), the pedicle screw angles from an anterolateral approach may be modified depending upon the anatomy of the particular segment of the spine. It should also be noted that the entry and termination/exit points of the pedicle screws may vary depending on the region of the spine, for example, the pedicle screw trajectory angles may be larger at S1 due to the larger vertebral body size. For example, in one embodiment a single contralateral screw placement is an option in the L5 and S1 vertebrae.

Figure 6:
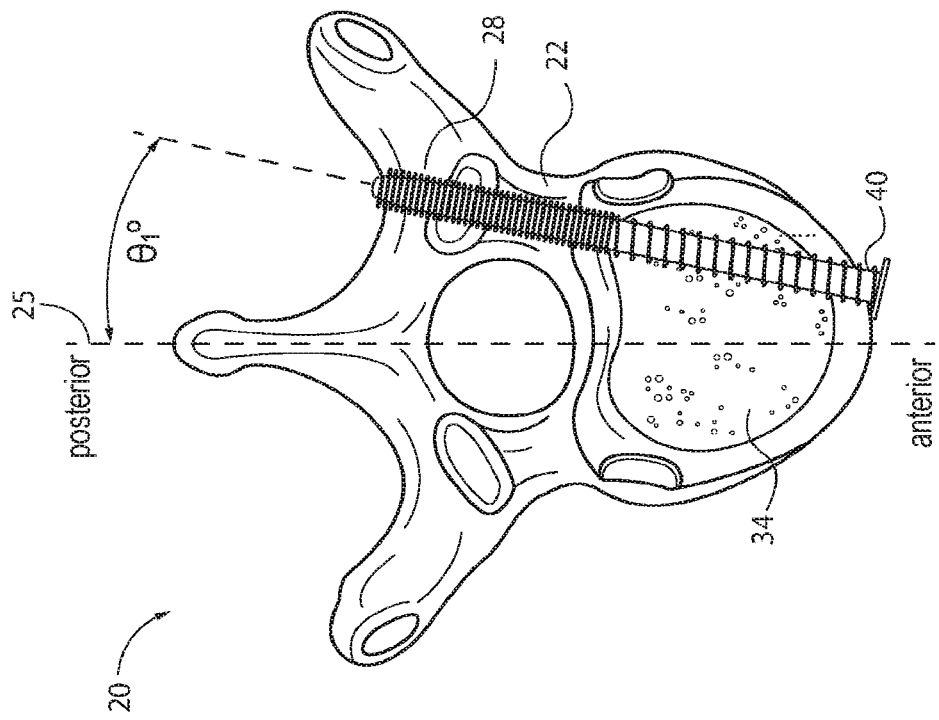
FIG. 6 is an axial planar view of a vertebra illustrating an example single pedicle screw having an anterior to posterior placement from an anterior approach according to an embodiment of the invention.

FIG. 6 is an axial planar view of a vertebra 20 illustrating an example single ipsilateral pedicle screw 40 having an anterior to posterior placement from an anterior approach according to an embodiment of the invention. In the illustrated embodiment, the pedicle screw 40 enters through the body 34 of the vertebra 20 and proceeds through the pedicle 22 and terminates in or near the lamina 28. The axial planar angle of entry $\theta_1°$ of ipsilateral pedicle screw 40 is in the range of about 180° to 200° or roughly about 190°. As will be discussed in more detail with respect to FIG. 12, pedicle screw 40 may have a sagittal angle in the range of 170°-220°.

Figure 7:
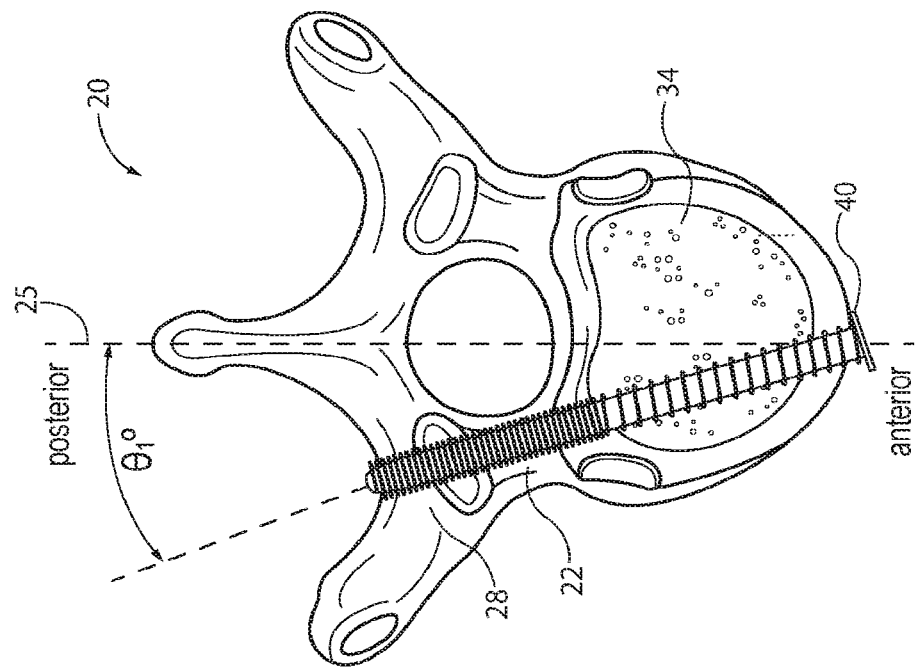
FIG. 7 is an axial planar view of a vertebra illustrating an example single pedicle screw having an anterior to posterior placement from an anterolateral approach according to an embodiment of the invention.

FIG. 7 is an axial planar view of a vertebra 20 illustrating an example single contralateral pedicle screw 40 having an anterior to posterior placement from an anterolateral approach according to an embodiment of the invention. In the illustrated embodiment, the pedicle screw 40 enters through the body 34 of the vertebra 20 and proceeds through the pedicle 22 and terminates in or near the lamina 28. The axial planar angle of entry $\theta_1°$ of contralateral pedicle screw 40 is in the range of about 140° to 160° or roughly about 150°. As will be discussed in more detail with respect to FIG. 12, pedicle screw 40 may have a sagittal angle in the range of 170°-220°.

In one embodiment, contralateral pedicle screw 40 is placed in the vertebra L4 or higher in the spine. The screw 40 is angled up, inferior to superior from the anterior (front) to the posterior (back) of the spine and follows a contralateral path is generally from the left anterior to the right posterior of the vertebra 20. Pedicle screw 40 is directed contralaterally across the vertebral body 34 and may exit the right post cortex of the vertebra 20 at the junction of the transverse process 26 and facet joint/superior articular process 24. In one embodiment, the entry point of the pedicle screw 40 into the vertebra 20 is approximately 1 cm to the left of the sagittal plane 25 and pierces the posterior cortex of the pedicle 22 at the superior articular process 24.

Figure 8:
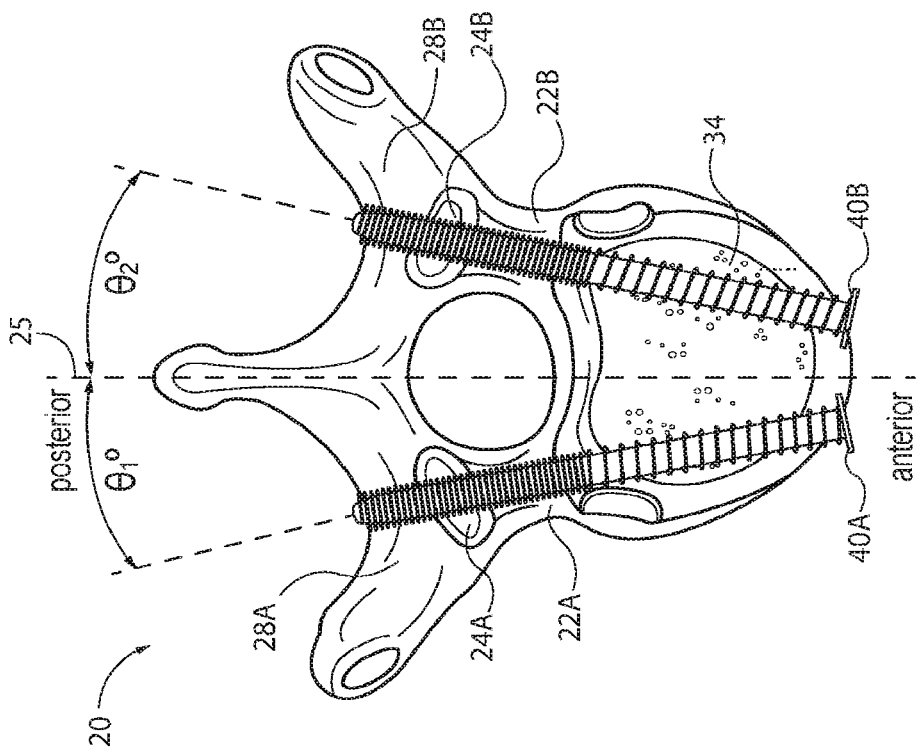
FIG. 8 is an axial planar view of a vertebra illustrating an example of dual pedicle screws having an anterior to posterior placement from an anterior approach according to an embodiment of the invention.

FIG. 8 is an axial planar view of a vertebra 20 illustrating an example of dual ipsilateral pedicle screws 40A and 40B having an anterior to posterior placement from an anterior approach according to an embodiment of the invention. In the illustrated embodiment, pedicle screw 40A enters through the body 34 of the vertebra 20 and proceeds through the pedicle 22A and terminates in or near the lamina 28A. The axial planar angle of entry θ1° of ipsilateral pedicle screw 40A is in the range of about 165° to 185° or roughly about 175°. As will be discussed in more detail with respect to FIG. 12, pedicle screw 40A may have a sagittal angle in the range of 170°-220°. Similarly, pedicle screw 40B enters through the body 34 of the vertebra 20 and proceeds through the pedicle 22B and terminates in or near the lamina 28B. The axial planar angle of entry $\theta_2°$ of ipsilateral pedicle screw 40B is in the range of about 180° to 200° or roughly about 190°. As will be discussed in more detail with respect to FIG. 12, pedicle screw 40B may have a sagittal angle in the range of 170°-220°.

In one embodiment, the ipsilateral pedicle screws 40A and 40B are placed in the spine at the S1 or L5 vertebra. Because the S1 and L5 vertebra are larger and because the surgical approach in this region is typically directly anterior, two pedicle screws 40A and 40B are employed. However, a single contralateral screw is also an option at the S1 or L5 vertebra. It should be noted that the sagittal angle for pedicle screws 40A and 40B in the S1 vertebra can be vary widely within the sagittal angle range.

In the illustrated embodiment, the ipsilateral pedicle screws 40A and 40B are on opposite sides of the sagittal plane 25. The entry points on each side of the vertebra 20 may be approximately 1 cm from the sagittal plane 25 (midline) at the anterior of the vertebra 20. Although pedicle screws 40A and 40B are shown as ipsilateral screws, at the S1 or L5 level pedicle screws may have a trajectory that is directly posterior, ipsilateral or contralateral such that they proceed through the body 34 along an axis of the pedicle from inferior to superior, piercing the posterior cortex of the vertebra 20 at the superior articular process 24 (i.e., the junction of the transverse process and the facet joint). In one embodiment, the vertebra 20 can be the L5 vertebra such as illustrated later with respect to FIGS. 14 and 15.

Figure 9:
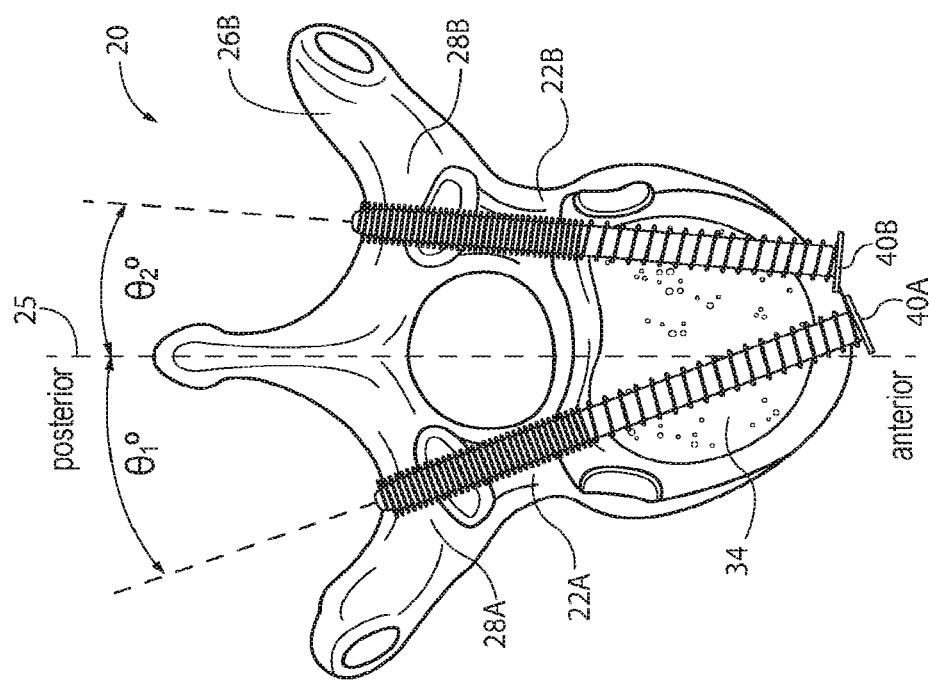
FIG. 9 is an axial planar view of a vertebra illustrating an example of dual pedicle screws having an anterior to posterior placement from an anterior approach and an anterolateral approach according to an embodiment of the invention.

FIG. 9 is an axial planar view of a vertebra illustrating an example of dual pedicle screws 40A and 40B having an anterior to posterior placement from an anterior approach and/or an anterolateral approach according to an embodiment of the invention. In the illustrated embodiment, contralateral pedicle screw 40A enters through the body 34 of the vertebra 20 and proceeds through the pedicle 22A and terminates in or near the lamina 28A. The axial planar angle of entry $\theta_1°$ of contralateral pedicle screw 40A is in the range of about 155° to 175° or roughly about 165°. As will be discussed in more detail with respect to FIG. 12, pedicle screw 40A may have a sagittal angle in the range of 170°-220°. Similarly, ipsilateral pedicle screw 40B enters through the body 34 of the vertebra 20 and proceeds through the pedicle 22B and terminates in or near the lamina 28B. The axial planar angle of entry $\theta_2°$ of ipsilateral pedicle screw 40B is in the range of about 180° to 200° or roughly about 190°. As will be discussed in more detail with respect to FIG. 12, pedicle screw 40B may have a sagittal angle in the range of 170°-220°.

In one embodiment, pedicle screws 40A and 40B are placed in the spine at the L4 or higher vertebra. In the illustrated embodiment, the ipsilateral trajectory of pedicle screw 40B enters at the left anterior side of vertebra 20 and proceeds through the body 34 and into the left pedicle 22B from inferior to superior. In one embodiment, the entry point may be approximately halfway between the sagittal plane 25 (midline) and the transverse process 26B. Accordingly, the ipsilateral screw 40B extends through the pedicle at more of an angle to its longitudinal axis (lateral to medial axis), and exits at a point which pierces the post cortex of the vertebra 20 at the junction of the facet and lamina 28.

Similarly, the contralateral trajectory of pedicle screw 40A enters the vertebra 20 at a point that is slightly more anterior and inferior on the lateral aspect of the vertebra 20. The contralateral trajectory generally starts on the left of the sagittal plane 25 (midline) and defines a contralateral path from the entry point in the anterior face of the vertebra 20 and proceeds through the body 34 and the pedicle 22A to exit the vertebra 20 between the transverse process 26A and facet joint.

Figure 10:
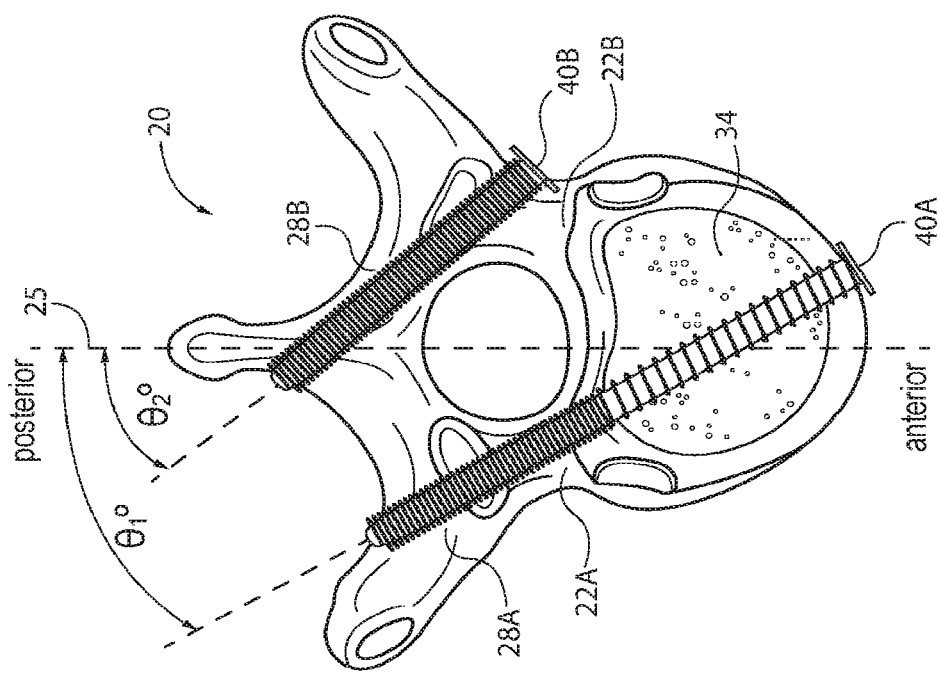
FIG. 10 is an axial planar view of a vertebra illustrating an example of dual pedicle screws having an anterior to posterior placement from an anterolateral approach according to an embodiment of the invention.

FIG. 10 is an axial planar view of a vertebra 20 illustrating an example of dual contralateral pedicle screws 40A and 40B having an anterior to posterior placement from an anterior approach and/or an anterolateral approach according to an embodiment of the invention. In the illustrated embodiment, contralateral pedicle screw 40A enters through the body 34 of the vertebra 20 and proceeds through the pedicle 22A and terminates in or near the lamina 28A. The axial planar angle of entry $\theta_1°$ of contralateral pedicle screw 40A is in the range of about 135° to 155° or roughly about 145°. As will be discussed in more detail with respect to FIG. 12, pedicle screw 40A may have a sagittal angle in the range of 170°-220°. Similarly, contralateral pedicle screw 40B enters near the pedicle 22B and does not pass through the body 34 of the vertebra 20. The contralateral pedicle screw 40B proceeds from the pedicle 22B through the lamina 28A and exits or terminates at or near the lamina 28A on the opposite side of the vertebra 20. The axial planar angle of entry $\theta_2°$ of contralateral pedicle screw 40B is in the range of about 115° to 125° or roughly about 115°. As will be discussed in more detail with respect to FIG. 12, pedicle screw 40B may have a sagittal angle in the range of 170°-220°.

Figure 11:
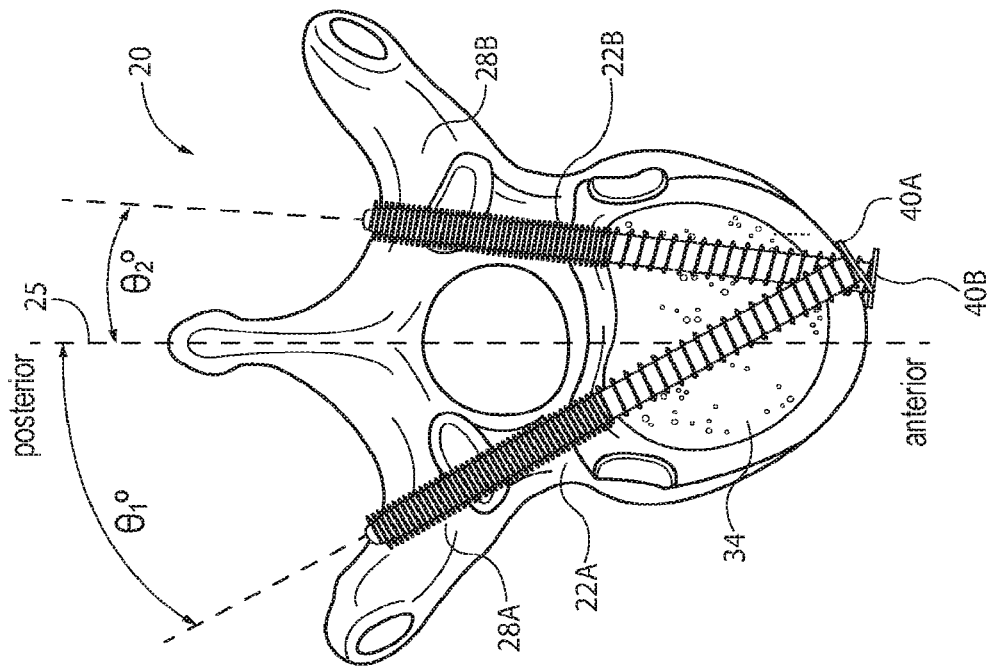
FIG. 11 is an axial planar view of a vertebra illustrating an example of dual pedicle screws having an anterior to posterior placement from an anterior approach and an anterolateral approach with crossing screw paths according to an embodiment of the invention.

FIG. 11 is an axial planar view of a vertebra illustrating an example of dual pedicle screws 40A and 40B having an anterior to posterior placement from an anterior approach and/or an anterolateral approach with transverse screw paths according to an embodiment of the invention. In the illustrated embodiment, contralateral pedicle screw 40A enters through the body 34 of the vertebra 20 and proceeds across the sagittal plane 25 and through the pedicle 22A and exits or terminates at or near the lamina 28A. The axial planar angle of entry $\theta_1°$ of contralateral pedicle screw 40A is in the range of about 135° to 155° or roughly about 145°. As will be discussed in more detail with respect to FIG. 12, pedicle screw 40A may have a sagittal angle in the range of 170°-2200. Similarly, ipsilateral pedicle screw 40B enters through the body 34 of the vertebra 20 and proceeds through the pedicle 22B and exits or terminates at or near the lamina 28B. The axial planar angle of entry θ2° of ipsilateral pedicle screw 40B is in the range of about 185° to 205° or roughly about 195°. As will be discussed in more detail with respect to FIG. 12, pedicle screw 40B may have a sagittal angle in the range of 170°-2200. In the illustrated embodiment, the pedicle screws 40A and 4B are transverse because their trajectories cross from the axial planar viewpoint.

In one embodiment, the transverse pedicle screws 40A and 40B are placed in the spine at the L4 vertebra or higher. In the illustrated embodiment, the transverse pedicle screws 40A and 40B comprise an ipsilateral trajectory of screw 40B with a contralateral trajectory of screw 40A. The contralateral screw 40A enters the vertebra 20 lower and to the left of the ipsilateral screw 40B. The contralateral screw 40A is also angled more steeply (sagittal angle) in an inferior to superior direction from anterior (front) to posterior (back) than the ipsilateral screw 40B. This advantageously provides necessary clearance between the screws 40A and 4B at the crossover position. Similarly, the ipsilateral screw 40B enters the vertebra 20 slightly higher and slightly more anterior than the contralateral screw 40A and has a shallower sagittal angle from anterior (front) to posterior (back).

In one embodiment, the pedicle screw lengths for ipsilateral trajectories range from approximately 35 to 55 cm, while the pedicle screw lengths for contralateral trajectories are longer, in a range from around 45 to 70 cm. The pedicle screw diameters are around 5.0-8.0 mm. The ipsilateral pedicle screws and shorter contralateral pedicle screws at the shorter end of the range may be standard off the shelf (OTS) pedicle screws, while longer pedicle screws (e.g. from 55 to 70 cm) designed for contralateral placement along paths outside the normal OTS pedicle screw length may be custom made in a range of sizes.

In the embodiments described above, the pedicle screws may exit or extend out of the posterior face of the respective pedicle, so as to obtain bi-cortical purchase. This increases their pullout strength. However, in some embodiments the ends of the screws may terminate within the pedicle close to the posterior face rather than piercing the posterior face or wall. The screw insertion technique may be similar to current screw insertion techniques in general spinal surgery. During surgery, fluoroscopy and/or intraoperative neuro-navigation equipment may be used to assist in guiding screw placement, for example using a neuro-surgical navigation and imaging system such as the Medtronic Stealth or Stealth Station® navigation system and O-arm® surgical imaging system or the like.

Conventional tools for placement of the screws may be used for most anterior screw entry points and anterior to posterior trajectories. However, a special 90-degree wrench may be needed to place certain pedicle screws that are difficult to place, for example when the surgical exposure is primarily lateral and on the left side of the subject and pedicle screw 40B is being placed.

Figure 12:
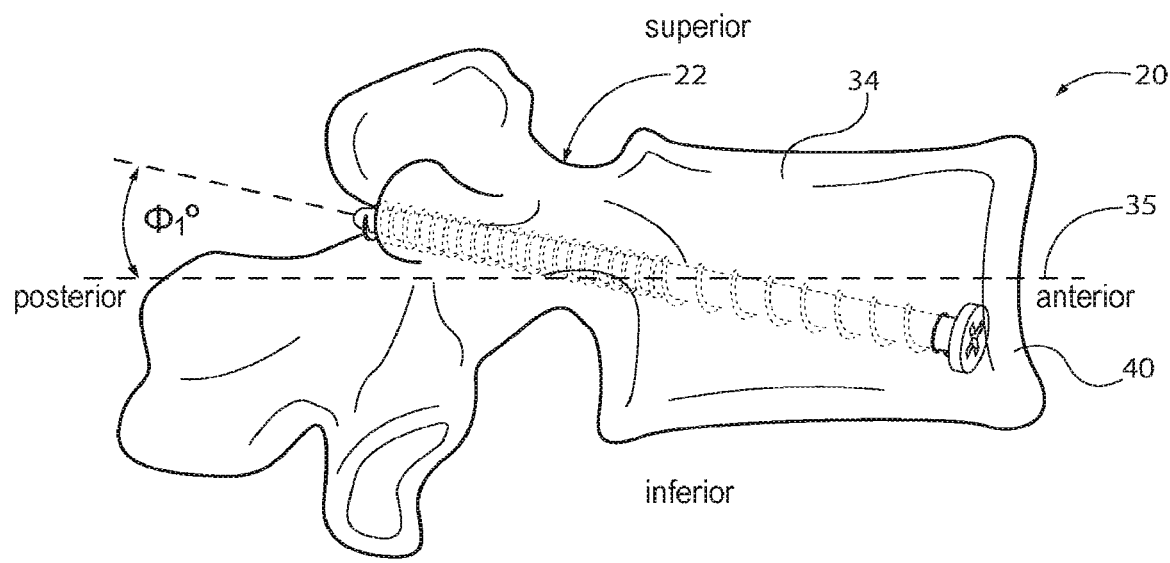
FIG. 12 is a sagittal plane view of a vertebra illustrating an example single pedicle screw having an anterior to posterior placement from an anterior approach or anterolateral approach with an upward inclination angle according to an embodiment of the invention.

FIG. 12 is a sagittal plane view of a vertebra 20 illustrating an example single pedicle screw having an anterior to posterior placement from an anterior approach or anterolateral approach with an upward inclination angle $\Phi1°$ according to an embodiment of the invention. In the illustrated embodiment, pedicle screw 40 enters the vertebra 20 at an inferior (lower) position with respect to the transverse plane 35 on the anterior side of the vertebra 20. The pedicle screw 40 proceeds through the vertebra 20 and passes upward through the body 34 to where it and exits or terminates at a superior (higher) position with respect to the transverse plane 35 on the posterior side of the vertebra 20. The sagittal angle of entry $\Phi1°$ of pedicle screw 40 is in the range of about 185° to 205° or roughly about 195°. The illustrated pedicle screw 40 in thesagittal plane view with its sagittal angle can be applied to any of the pedicle screws illustrated in FIGS. 6-11.

Figure 13:
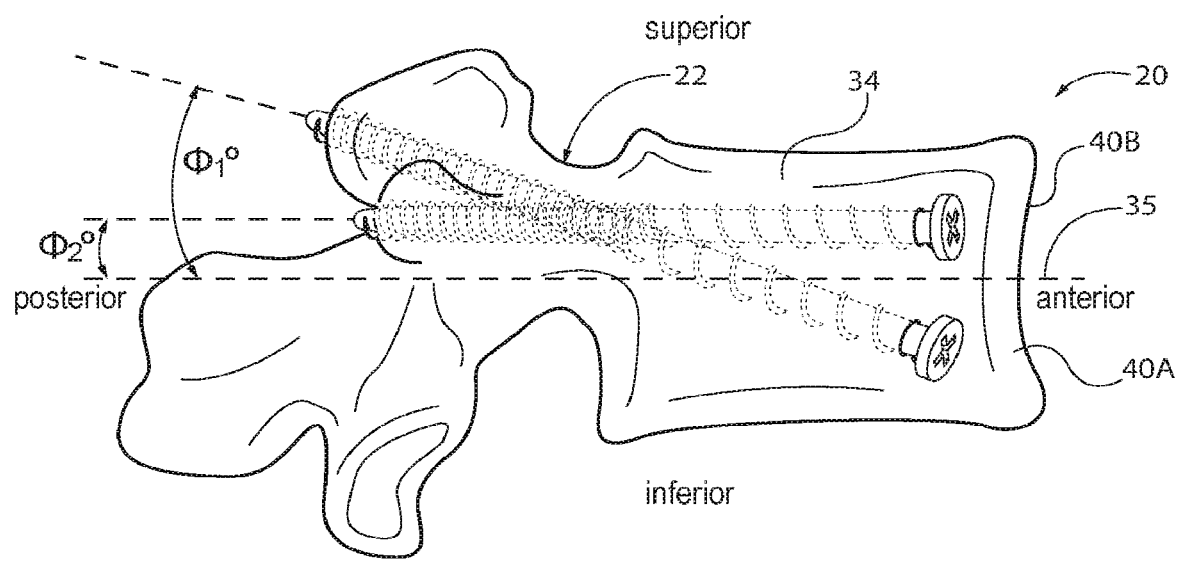
FIG. 13 is a sagittal plane view of a vertebra illustrating an example of dual pedicle screws having an anterior to posterior placement with or without crossing screw paths from an anterior approach or anterolateral approach with an upward inclination angle according to an embodiment of the invention.

FIG. 13 is a sagittal plane view of a vertebra 20 illustrating an example of dual pedicle screws 40A and 40B having an anterior to posterior placement with or without transverse (from the axial planar viewpoint) screw paths from an anterior approach or anterolateral approach with respective upward inclination angles $\Phi1°$ and $\Phi2°$ according to an embodiment of the invention. In the illustrated embodiment, pedicle screw 40A enters the vertebra 20 at an inferior (lower) position with respect to the transverse plane 35 on the anterior side of the vertebra 20. The pedicle screw 40A proceeds through the vertebra 20 and passes upward through the body 34 to where it exits or terminates on the posterior side of the vertebra 20. The pedicle screw 40A may exit or terminate at a superior (higher) position with respect to the transverse plane 35 or at the transverse plane 35 or at an inferior (lower) position with respect to the transverse plane 35. The sagittal angle of entry $\Phi1°$ of pedicle screw 40A is in the range of about 195° to 215° or roughly about 205°.

Similarly, pedicle screw 40B enters the vertebra 20 at a superior (higher) position with respect to pedicle screw 40A on the anterior side of the vertebra 20. It should be noted that although the pedicle screw 40B is shown to enter superior to the transverse plane 35, it may also enter the vertebra inferior to the transverse plane 35 while still being superior to the pedicle screw 40A. The pedicle screw 40B proceeds through the vertebra 20 and passes directly (straight) or upward or downward through the body 34 to where it exits or terminates on the posterior side of the vertebra 20. The pedicle screw 40B may exit or terminate at a superior (higher) position with respect to the transverse plane 35 or at the transverse plane 35 or at an inferior (lower) position with respect to the transverse plane 35. The sagittal angle of entry $\Phi2°$ of pedicle screw 40B is in the range of about 170° to 190° or roughly about 180°.

The illustrated pedicle screws 40A and 40B in the present sagittal plane view with their respective sagittal angles can be applied to any of the dual pedicle screw embodiments illustrated in FIGS. 6-11.

Figure 14:
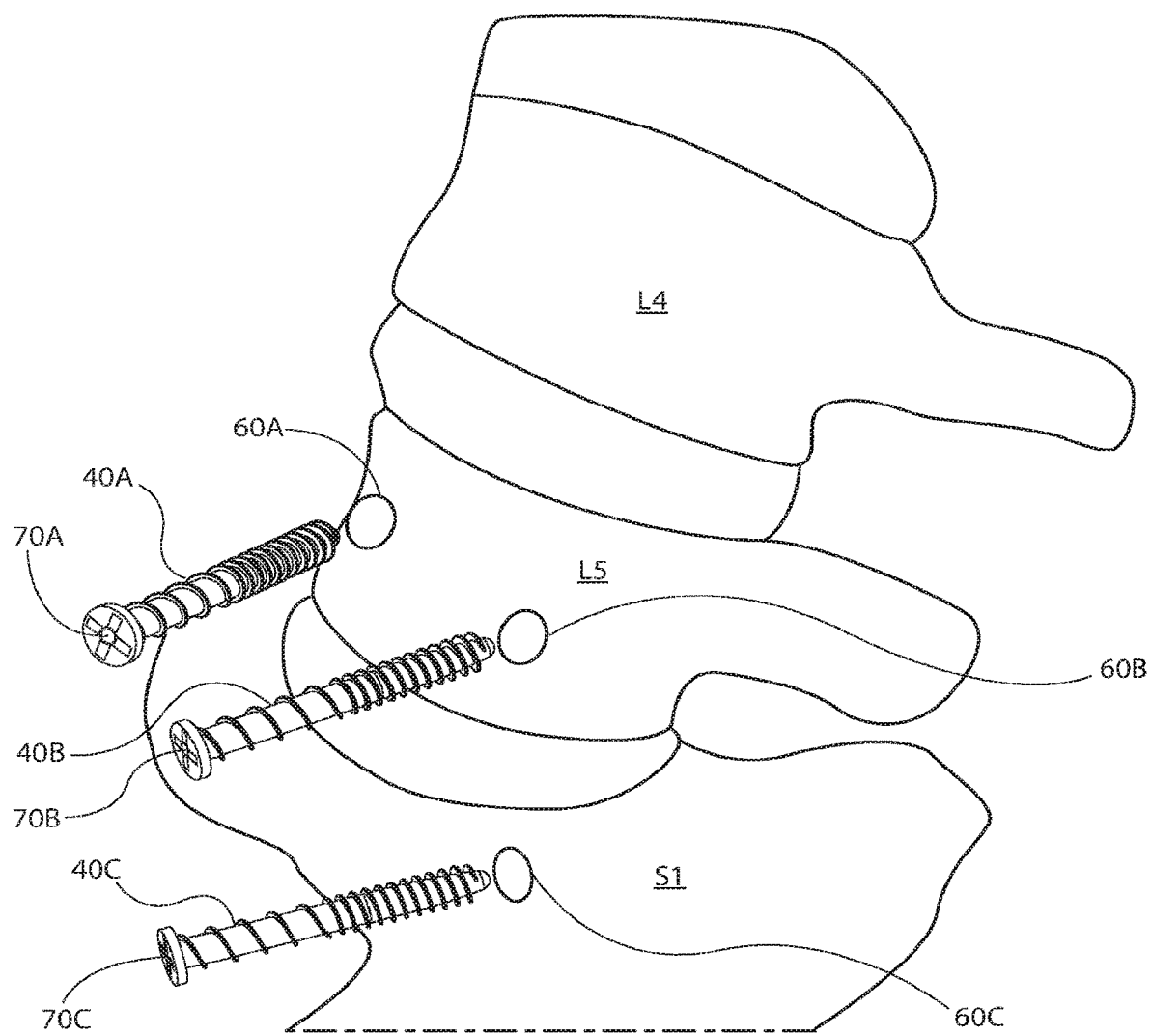
FIG. 14 is an anterolateral perspective view of anterior to posterior pedicle screw trajectories in the lumbar L5 vertebra and sacral S1 vertebra according to an embodiment of the invention.
Figure 15:
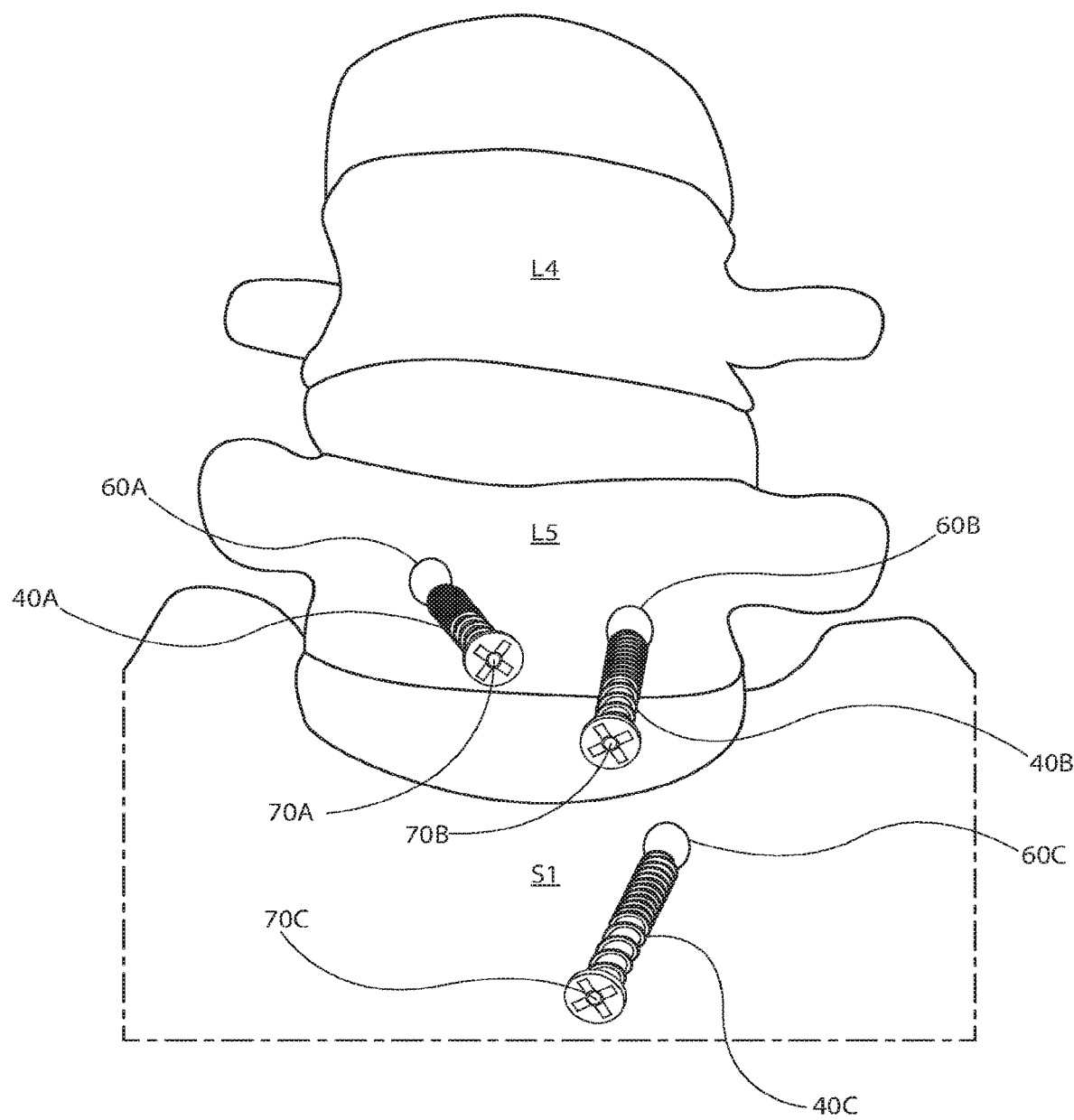
FIG. 15 is an anterior perspective view of anterior to posterior pedicle screw trajectories in the lumbar L5 vertebra and sacral S1 vertebra according to an embodiment of the invention.

FIGS. 14 and 15 are alternative views of anterior to posterior trajectories for pedicle screws 40A, 40B and 40C in the lumbar L5 vertebra and sacral S1 vertebra according to an embodiment of the invention. In alternative embodiments, the trajectories of the two pedicle screws 40A, 40B in the L5 vertebra can be the same as shown in FIGS. 8, 9, 10, 11, and/or 13.

FIG. 14 provides a perspective view while FIG. 15 provides an anterior view. In the illustrated embodiments, pedicle screw 40A having a threaded inner channel 70A enters the L5 vertebra through pre-drilled entry hole 60A and pedicle screw 40B having a threaded inner channel 70B enters the L5 vertebra through pre-drilled entry hole 60B and pedicle screw 40C having a threaded inner channel 70C enters the S1 vertebra through pre-drilled entry hole 60C. Advantageously, the same or similar entry positions and trajectories may be used in higher vertebra and higher regions of the spine. In various embodiments, one or two screws may be placed in each vertebra to be used for spinal stabilization at the spinal surgery location, depending on the level of the spine on which the operation is taking place.

In the illustrated embodiment, entry holes 60A and 60B are each spaced approximately one centimeter way from the sagittal plane (midline) of the L5 vertebra on the anterior of the vertebra L5. The pedicle screws 40A and 40B in the vertebra L5 are ipsilateral and thus have trajectories that place them into respective pedicles of the vertebra L5 on the same side of the sagittal plane (midline) as the corresponding entry holes 60A and 60B.

In the illustrated embodiment, pedicle screws 40A and 40B are substantially aligned horizontally to facilitate convenient attachment to the pedicle screws of fixation devices such as posts or rods or plates. Similarly, pedicle screws 40B and 40C are substantially aligned vertically to facilitate convenient attachment to the pedicle screws of fixation devices such as posts or rods or plates.

It should be noted that the S1 pedicle is so large that a range of angles may be used for insertion of the pedicle screw 40C through the vertebra S1 and into the pedicle, based on the easiest approach angle consistent with appropriate alignment with the pedicle screws 40A and/or 40B that are positioned in L5 vertebra. In various embodiments, one or more pedicle screws may be placed in the S1 vertebra. The pedicle screw 40C placed in an anterior to posterior direction in the S1 vertebra may follow a similar or identical trajectory as either of pedicle screws 40A and 40B described above. The pedicle screw 40C placed in an anterior to posterior direction in the S1 vertebra may also follow a completely different trajectory (e.g., contralateral) as the pedicle screws 40A and 40B.

Figure 16:
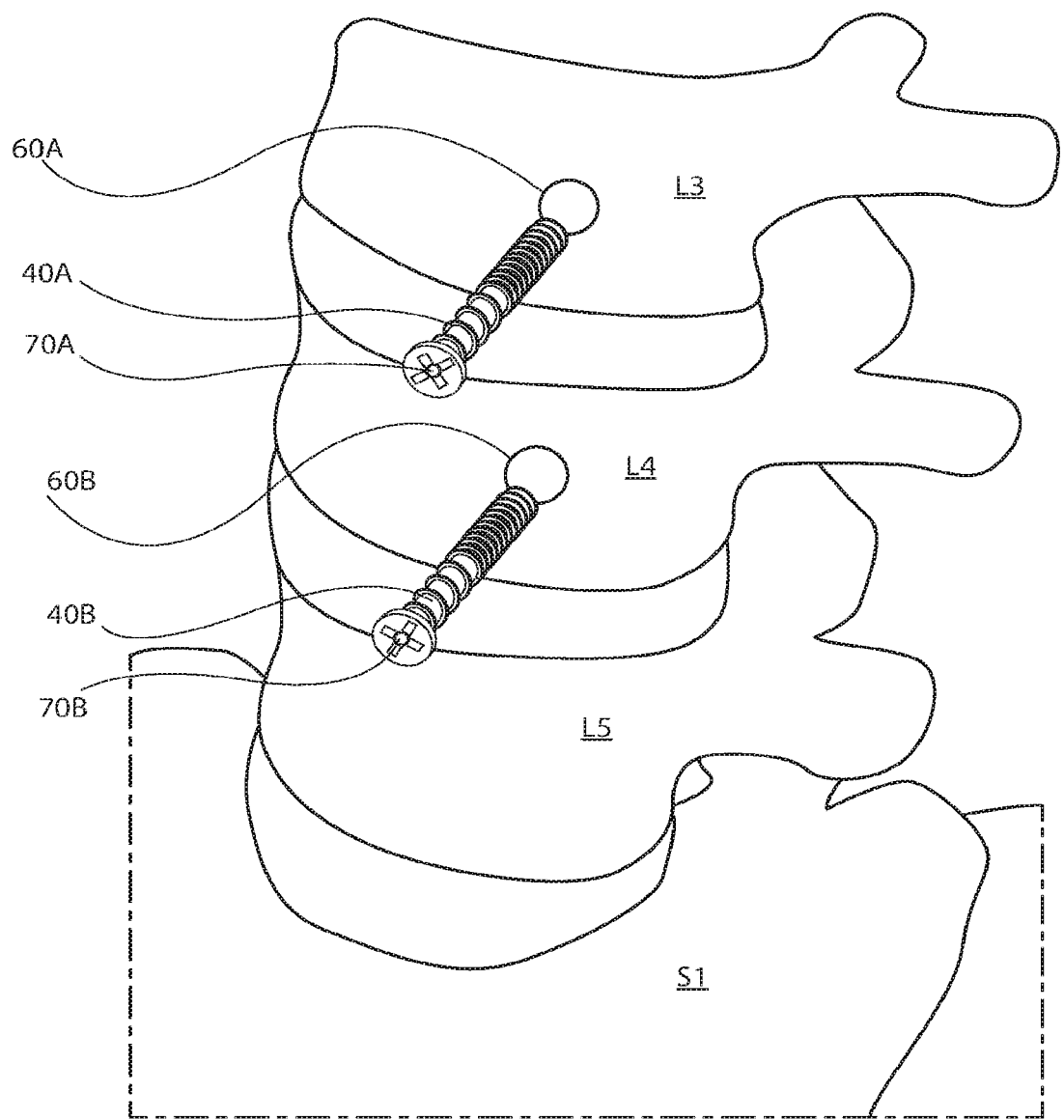
FIG. 16 is a lateral perspective view of anterior to posterior pedicle screw trajectories in the lumbar L5 vertebra and sacral S1 vertebra according to an embodiment of the invention.

FIG. 16 is a perspective view of example anterolateral pedicle screw trajectories for pedicle screws 40A and 40B, each having a respective threaded inner channel 70A and 70B. The pedicle screws 40A and 40B are inserted into the lumbar L3 and L4 vertebrae according to an embodiment of the invention. In the illustrated embodiments, pedicle screw 40A enters the L3 vertebra through pre-drilled entry hole 60A and pedicle screw 40B enters the L4 vertebra through pre-drilled entry hole 60B. Advantageously, pedicle screws 40B and 40C are substantially aligned vertically to facilitate convenient attachment to the pedicle screws of fixation devices such as posts or rods or plates. For example, the orientation of pedicle screws 40A and 40B may allow for a slotted plate to be secured to each of the pedicle screws for spinal stabilization and improved biomechanical strength.

In various embodiments, one or more pedicle screws may be placed in vertebra L4 or in vertebra in higher regions of the spine, depending on spinal anatomy and surgical exposure. In one embodiment, the pedicle screw entry hole 60B in vertebra L4 is approximately halfway between the sagittal plane (midline) of the L4 vertebra and the transverse process of the lateral aspect of the vertebra (generally from the left side, as indicated by pedicle screw 40B. In one embodiment, the trajectory of pedicle screw 40B is contralateral, which causes the pedicle screw to extend across the vertebral body from the entry point on the anterior left side to a termination/exit point on the posterior right side. In the illustrated embodiment, the trajectory of pedicle screw 40B has an axial planar angle in the range of 125° to 145° or roughly 135°. The illustrated trajectory, determined by the axial planar angle and the sagittal angle, causes the pedicle screw 40B to traverse the contralateral pedicle from inferior to superior and from medial to lateral, exiting the right post cortex of the vertebra at the junction of the transverse process and facet joint/superior articular process or terminating prior to exiting.

Figure 17:
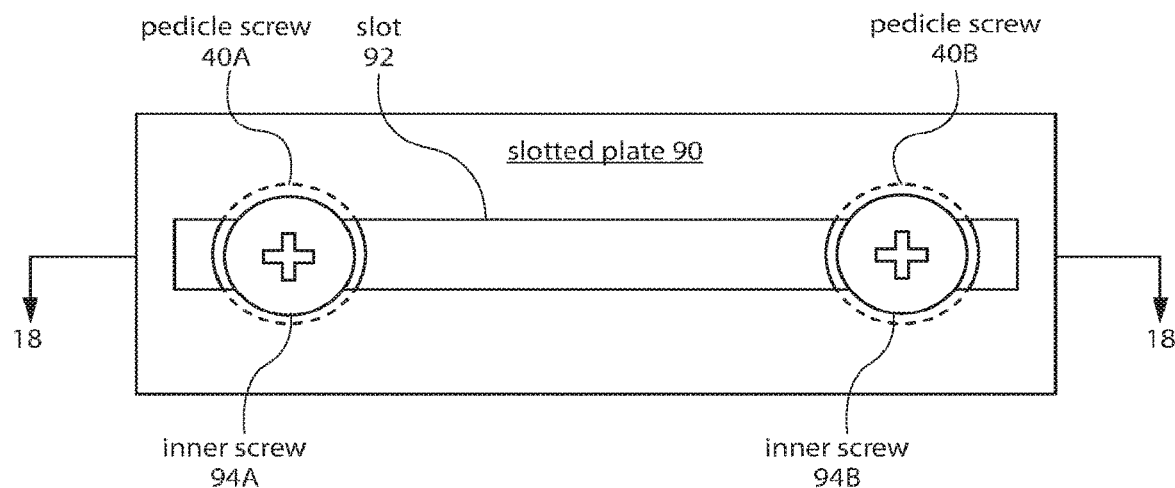
FIG. 17 is a top view of a very low profile slotted plate with pedicle screws and inner screws according to an embodiment of the invention.

FIG. 17 is a top view of a very low profile slotted plate 90 with pedicle screws 40A, 4B and inner screws 94A, 94B according to an embodiment of the invention. In the illustrated embodiment, the slotted plate 90 is generally rectangular, but may alternatively have another shape such as oval. The slotted plate 90 includes one or more through holes or slots 92 that extend through the front and back surfaces of the slotted plate 90. The single illustrated slot 92 begins near a first end of the slotted plate 90 and ends near a second end of the slotted plate 90. Alternatively, the slotted plate 90 may have plural slots arranged end-to-end or side-to-side or any combination of positions. The function of the slotted plate 90 is to join two or more pedicle screws. The purpose of the one or more slots 92 is to allow an inner screw such as inner screw 94A, to be threaded into the threaded inner channel 70A of a pedicle screw such as pedicle screw 40A. In this fashion, the head of the inner screw 94A clamps the slotted plate 90 to the head of the pedicle screw 40A to affix the slotted plate 90 to the vertebra.

Figure 18:
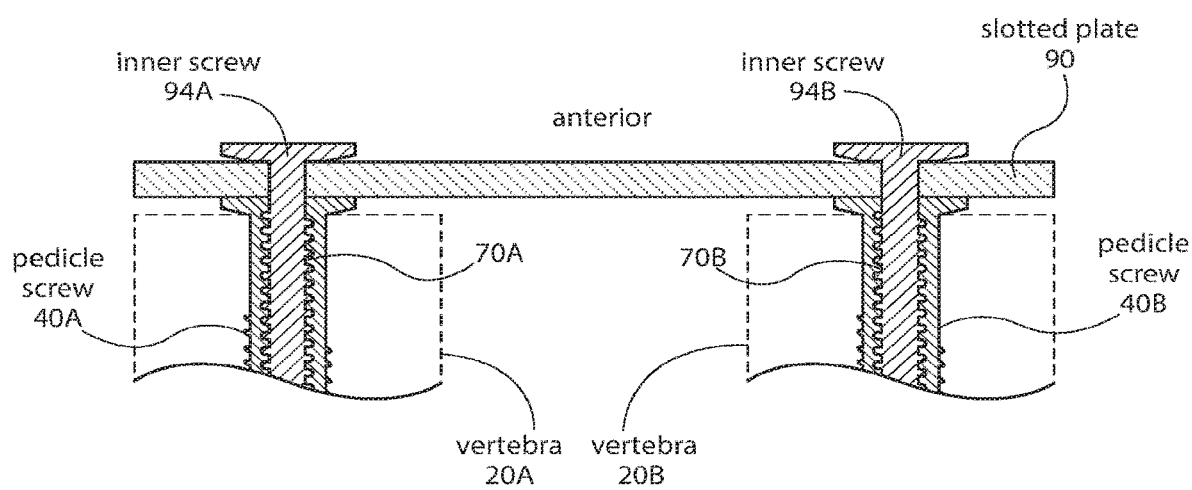
FIG. 18 is a cross sectional side view of the very low profile slotted plate of FIG. 17 with pedicle screws and inner screws according to an embodiment of the invention.

FIG. 18 is a cross sectional side view of the very low profile slotted plate 90 of FIG. 17 along line 18 with pedicle screws 40A, 40B and inner screws 94A, 94B according to an embodiment of the invention. In the illustrated embodiment, the slotted plate 90 is positioned on top of the flat heads of the pedicle screws 40A, 40B and is held in place by downward pressure applied by the underside of the head of inner screws 94A, 94B. The pedicle screws 40A, 40B are positioned in their respective vertebra 20A, 20B and each pedicle screw 40A, 40B has its respective threaded inner channel 70A, 70B into which the inner screws 94A, 94B are placed. In one embodiment, the width of the inner screws 94A, 94B is about two-thirds (⅔) of the width of the pedicle screws 40A, 40B. In alternative embodiments, an inner screw 94A may have a range of widths relative to its corresponding pedicle screw 40A. One factor that may determine the desired width of the inner screw include the desired combined biomechanical strength of the combined pedicle screw 40A and inner screw 94A when the two are threaded together. Additionally, the depth of the threaded inner channel 70A may also vary in alternative embodiments. Advantageously, when threaded into the pedicle screw 40A, the inner screw 94A may extend all the way to the bottom of the threaded inner channel 70A or it may extend a small portion or a large portion of the way to the bottom of the threaded inner channel 70A. The function of the inner screw 94A is to thread deep enough into the threaded inner channel 70A so that it will secure the slotted plate 90 to the vertebra. In one embodiment, the inner screw 94 has narrow pitched threads, similar to a machine screw.

Figure 19:
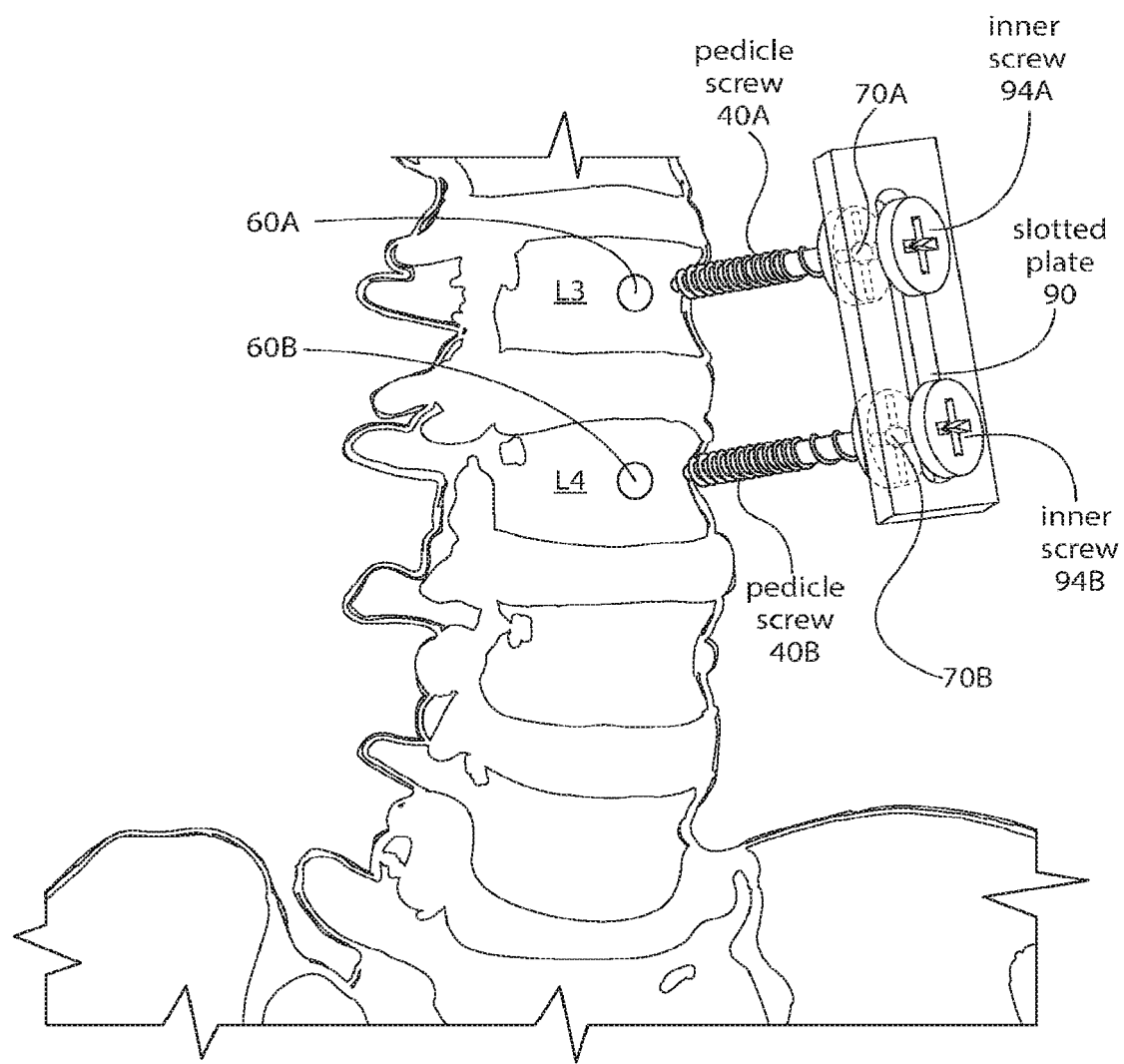
FIG. 19 is a perspective view of a very low profile slotted plate with pedicle screws and inner screws according to an embodiment of the invention.

FIG. 19 is a perspective view of a very low profile slotted plate 90 with pedicle screws 40A, 40B and inner screws 94A, 94B according to an embodiment of the invention. In the illustrated embodiment, pedicle screws 40A, 40B are shown having a primarily anterior trajectory into their respective vertebra L3 and L4 through pre-drilled holes 60A, 60B. Slotted plate 90 is secured to the flat top of the pedicle screws 40A, 40B by inner screws 94A, 94B.

Although the slotted plate 90 is shown secured to the pedicle screws 40A, 40B with the pedicle screws 40A, 40B not yet screwed into their respective vertebra L3, L4, in practice the pedicle screws 40A, 40B are first screwed into the pre-drilled holes 60A, 60B and then the slotted plate 90 is arranged over the pedicle screws 40A, 40B and the inner screws 94A, 94B are threaded into the threaded inner channel 70A, 70B of their respective pedicle screws 40A, 40B.

FIG. 20 is an axial planar view of a vertebra 20 illustrating an example anterior to posterior placement from an anterolateral approach of a pedicle screw 40 attached to a slotted plate 90 by an inner screw 94A according to an embodiment of the invention. In the illustrated embodiment, the pedicle screw 40 is positioned in the vertebra 20 with the flat head of the pedicle screw 40 on or near the outer surface of the vertebra 20. In one embodiment, the flat head of the pedicle screw 40 may be countersunk into the vertebra 20. Alternatively, the flat head of the pedicle screw 40 is above the external surface of the vertebra 20.

The inner screw 94A passes through a slot in the slotted plate 90 and is threaded into the threaded inner channel 70 of the pedicle screw 70 to secure the slotted plate to the vertebra 20. The slotted plate may advantageously extend up or down to an adjacent or other vertebra along the spine and be secured to a pedicle screw at that location to further stabilize the spine.

FIG. 21A is a plan view diagram of a distal cortical thread pitch pedicle screw 50 according to the invention. In the illustrated embodiment, the pedicle screw 50 comprises a head section 56 and a body section including a cortical pitch portion 52 and a coarse pitch portion 54. In the illustrated embodiment, the cortical pitch portion 52 is proximal the piercing tip of the pedicle screw 50. This is precisely opposite of standard convention pedicle screws such as previously described with respect to FIGS. 3, 4A and 4B. Also, in the illustrated embodiment, the distal cortical thread pitch pedicle screw 50 has a saddle structure as the head section 56.

Advantageously, the illustrated distal cortical thread pitch pedicle screw 50 is configured such that the cortical pitch portion 52 is situated in the pedicle bone of the vertebra when inserted using the generally anterior-to-posterior approach described herein. One advantage of the illustrated distal cortical thread pitch pedicle screw 50 is that when the cortical screw threads are positioned in the pedicle, which is made of cortical bone, the pull out strength of the distal cortical thread pitch pedicle screw 50 is significantly increased.

FIG. 21B is a plan view diagram of a distal cortical thread pitch pedicle screw 50 according to the invention. In the illustrated embodiment, the pedicle screw 50 comprises first end, a body section (52,54) and a head section 56 at a second end. The head section 56 has a diameter that is larger than the body section (52,54). The body section (52,54) includes a cortical pitch portion 52 and a coarse pitch portion 54. In the illustrated embodiment, the cortical pitch portion 52 is proximal the first end (i.e., the piercing tip) of the pedicle screw 50, similar to FIG. 21A and the coarse pitch portion 54 is proximal the head section 56. Also, in the illustrated embodiment, the distal cortical thread pitch pedicle screw 50 has a flat structure as the head section 56. The flat structure is advantageous for securing low profile plates to the vertebra, for example by way of an inner screw that extends through a through hole or slot in the plate such that the inner screw is threaded into a threaded inner channel of the pedicle screw 50.

FIG. 22 is a flow diagram illustrating an example process for connecting two pedicle screws with a plate according to the invention. Initially, in step 100, a receiving channel is drilled into the vertebra in the conventional manner to produce a hole in the vertebra into which the piercing tip of the pedicle screw may be inserted. Next, in step 105 a flat headed pedicle screw with a threaded inner channel is inserted into the hole and screwed into the receiving channel by twisting the pedicle screw down into the vertebra. In one embodiment, this may be accomplished using a 90 degree wrench to ensure the proper trajectory of the pedicle screw from the anterior or anterolateral approach. Next, in step 110 a slotted plate is placed over the top of the flat head portion of the pedicle screw such that the threaded inner channel is accessible to an inner screw through a slot in the slotted plate. Finally, in step 115 the inner screw is threaded down into the threaded inner channel to secure the slotted plate to the flat head of the pedicle screw.

The above method for pedicle screw placement may be used for stabilization of sacral, lumbar, thoracic and cervical spine regions, with appropriate adjustment of pedicle screw lengths and angles of approach based on size of the vertebra. The anterior to posterior pedicle screw fixation and bi-cortical purchase of the placed pedicle screws in the fixation assembly provides enhanced biomechanical strength and stabilization of all three columns of the spine via a single operation and spinal exposure on one side only. The above screw placement trajectories provide a method of stabilization of the spine through a single surgical exposure and approach in one operation, with pedicle screws placed into the spine and then the pedicle in a generally anterior, lateral, anterolateral, diagonal, or transverse to posterior trajectory, avoiding the need for a second operation exposing the posterior spine. This technique may be used for placement at any desired spinal surgery site including the sacral, lumbar, thoracic and cervical spine. Once screws have been placed, fixation devices such as plates, rods, and the like may be used to connect the screws from one vertebra to the next. These fixation devices may be modified if necessary to accommodate different screw positions.

Pedicle screw placement as described above allows both spinal stabilization surgery and pedicle screw placement to take place in a single surgical exposure, while the anterior, anterolateral or anterior/lateral spine is exposed. In the initial spinal stabilization surgery, implants, discs, and other stabilization devices may be placed in the spine after anterior, anterolateral or anterior/lateral surgical exposure of the spine. In the above embodiments, pedicle screws are placed into the spine and then the pedicle from the front of the spine to the back after completion of the initial spinal stabilization surgery, during the same surgery and using the same surgical exposure. The pedicle screws are inserted in a generally anterior, lateral, anterolateral, diagonal, or transverse to posterior trajectory, avoiding the need for a second operation exposing the posterior spine.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter that is broadly contemplated by the present invention. It is further understood that the scope of the present invention fully encompasses other embodiments that may become obvious to those skilled in the art.

What is claimed is:

1. A system comprising:
one or more pedicle screws having a first end, a body and a head at a second end, the one or more pedicle screws comprising a cortical pitch portion of the body proximal the first end of the pedicle screw and a coarse pitch portion of the body proximal the head of the pedicle screw;
one or more fixation devices directly attached to the head of the pedicle screw;
wherein at least one of the one or more pedicle screws comprises a threaded inner channel; and
an inner screw having a body and a head, wherein the head has a diameter greater than the body and wherein the inner screw is configured to be threaded into the inner channel, wherein the head of the inner screw is directly attached to the one or more fixation devices;
wherein the one or more fixation devices comprises at least one through hole configured to allow the body of the inner screw to pass through and prevent the head of the inner screw from passing through the through hole;
wherein the one or more pedicle screws are entirely located on one side of the one or more fixation devices and not passed through the through hole;
wherein the head of the inner screw is located at a first side of the one or more fixation devices and the head of the one or more pedicle screws is located at an opposed second side of the one or more fixation devices opposite to the first side;
wherein the fixation device has a bone facing surface and a directly opposite outer surface, wherein the outer surface is completely flat and defines the first side of the one or more fixation devices.

2. The system of claim 1, wherein the cortical pitch portion of the pedicle screw body is configured to engage the cortical bone of a pedicle when placed into a vertebra at a predetermined entry point on an anterior surface of the vertebra.

3. The system of claim 1, wherein the cortical pitch portion of the pedicle screw body is configured to engage the cortical bone of a pedicle when placed into a vertebra at a predetermined entry point on a lateral surface of the vertebra.

4. The system of claim 1, wherein the cortical pitch portion of the pedicle screw body is configured to engage the cortical bone of a pedicle when placed into a vertebra at a predetermined entry point on an anterolateral surface of the vertebra.

5. The system of claim 1, wherein the one or more fixation devices comprises: a planar plate.

6. The system of claim 5, wherein the one or more fixation devices is intercalated between the head of the inner screw and the head of the one or more pedicle screws, the fixation device is placed entirely between the head of the inner screw and the head of the pedicle screw.

7. The system of claim 6, wherein the head of the inner screw is spaced from the head of the one or more pedicle screws.

8. The system of claim 7, wherein the head of the inner screw is parallel to the head of the one or more pedicle screws, wherein a top of the head of the inner screw is flat.

9. A system comprising:
one or more pedicle screws having a first end, a body and a head at a second end, the one or more pedicle screws comprising a cortical pitch portion of the body proximal the first end of the pedicle screw and a coarse pitch portion of the body proximal the head of the pedicle screw;
one or more fixation devices directly attached to the head of the pedicle screw;
wherein at least one of the one or more pedicle screws comprises a threaded inner channel; and
an inner screw having a body and a head, wherein the head has a diameter greater than the body and wherein the inner screw is configured to be threaded into the inner channel, wherein the head of the inner screw is directly attached to the one or more fixation devices;
wherein the one or more fixation devices comprises at least one through hole configured to allow the body of the inner screw to pass through and prevent the head of the inner screw from passing through the through hole;
wherein the one or more pedicle screws are entirely located on one side of the one or more fixation devices and not passed through the through hole;
wherein the head of the inner screw is located at a first side of the one or more fixation devices and the head of the one or more pedicle screws is located at an opposed second side of the one or more fixation devices opposite to the first side;
wherein the fixation device has a bone facing surface and a directly opposite outer surface, wherein the outer surface is completely flat and defines the first side of the one or more fixation devices;
the fixation device is placed entirely between the head of the inner screw and the head of the pedicle screw;
wherein a top of the head of the inner screw is flat.

* * * * *